US012810993B2

(12) United States Patent
Hatsutani et al.

(10) Patent No.: US 12,810,993 B2
(45) Date of Patent: Nov. 24, 2026

(54) INFORMATION PROCESSING APPARATUS, INFORMATION PROCESSING METHOD, AND PROGRAM FOR CREATING DOCUMENT INCLUDING IMAGE AND SENTENCE

(71) Applicant: FUJIFILM Corporation, Tokyo (JP)

(72) Inventors: Taro Hatsutani, Tokyo (JP); Aya Ogasawara, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 261 days.

(21) Appl. No.: 18/592,396

(22) Filed: Feb. 29, 2024

(65) Prior Publication Data

US 2024/0296934 A1 Sep. 5, 2024

(30) Foreign Application Priority Data

Mar. 3, 2023 (JP) ................................ 2023-033155

(51) Int. Cl.
*G16H 30/20* (2018.01)
*G06T 7/00* (2017.01)
*G16H 15/00* (2018.01)

(52) U.S. Cl.
CPC .......... *G16H 30/20* (2018.01); *G06T 7/0016* (2013.01); *G16H 15/00* (2018.01)

(58) Field of Classification Search
None
See application file for complete search history.

(56) References Cited

U.S. PATENT DOCUMENTS 11,075,003 B2 7/2021 Sakamoto et al.
2010/0256459 A1 10/2010 Miyasa et al.
(Continued)

FOREIGN PATENT DOCUMENTS

CN 113990431 A * 1/2022 .......... G06F 40/216
JP 2009082441 4/2009
(Continued)

OTHER PUBLICATIONS

Yu, H., Yao, F., Lu, W., Liu, N., Li, P., You, H., & Sun, X. (2022). Text-image matching for cross-modal remote sensing image retrieval via graph neural network. IEEE Journal of Selected Topics in Applied Earth Observations and Remote Sensing, 16, 812-824. (Year: 2022).*

(Continued)

*Primary Examiner* — Siamak Harandi
*Assistant Examiner* — Annie H Pham
(74) *Attorney, Agent, or Firm* — JCIPRNET

(57) ABSTRACT

Provided are an information processing apparatus, an information processing method, and a program that reduce an error in making an image correspond to a sentence of a document including sentences and images and/or create a document that is easy to read as compared with an original document. At least one processor and at least one memory that stores a command to be executed by the at least one processor are provided, in which the at least one processor is configured to acquire information regarding an object shown in one or more received images, acquire information described in one or more received sentences, determine presence or absence of correspondence between the image and the sentence based on the information regarding the object and the described information, and execute processing of assisting in creating a document including the image and the sentence based on the presence or absence of the correspondence.

17 Claims, 17 Drawing Sheets

(56) References Cited

U.S. PATENT DOCUMENTS

| | | | | |
|---|---|---|---|---|
| 2015/0262014 | A1 | 9/2015 | Iwamura et al. | |
| 2022/0051771 | A1* | 2/2022 | Lyman | G06F 16/245 |
| 2023/0005580 | A1* | 1/2023 | Momoki | G16H 50/30 |
| 2023/0253083 | A1* | 8/2023 | Shibuya | G16H 15/00<br>382/128 |

FOREIGN PATENT DOCUMENTS

| | | | | | |
|---|---|---|---|---|---|
| JP | 2010160590 | A | * | 7/2010 | |
| JP | 2015187845 | | | 10/2015 | |
| JP | 2016057695 | | | 4/2016 | |
| JP | 2016057695 | A | * | 4/2016 | A61B 6/032 |
| JP | 2020149682 | A | * | 9/2020 | |
| JP | 6923863 | | | 8/2021 | |

OTHER PUBLICATIONS

“Notice of Reasons for Refusal of Japan Counterpart Application”, issued on Sep. 16, 2026, with English translation thereof, p. 1-p. 8.

* cited by examiner

INFORMATION PROCESSING APPARATUS, INFORMATION PROCESSING METHOD, AND PROGRAM FOR CREATING DOCUMENT INCLUDING IMAGE AND SENTENCE

CROSS-REFERENCE TO RELATED APPLICATION

The present application claims priority under 35 U.S.C § 119 (a) to Japanese Patent Application No. 2023-033155 filed on Mar. 3, 2023, which is hereby expressly incorporated by reference, in its entirety, into the present application.

BACKGROUND OF THE INVENTION

1. Field of the Invention

The present invention relates to an information processing apparatus, an information processing method, and a program, and particularly relates to a technique of assisting in creating a document including sentences and images.

2. Description of the Related Art

A doctor creates a key image for important findings in a case of creating an interpretation report. The key image is created such that another doctor can quickly check a status and position of a lesion in a case of reading the interpretation report, and is created as a reference in a case where an image of the same patient is interpreted in the future.

In creating the key image, the doctor needs to perform works such as checking whether the key image of the important findings has been created, rearrangement of an order of interpretation reports and an order of key images to make the orders the same, and insertion of a figure number into the interpretation report.

However, these works are burdensome, and may cause problems such as mismatch between the order of the interpretation reports and the order of the key images, presence of an unnecessary key image, and presence of a key image with omission of description.

JP2016-057695A discloses a technique for acquiring a region of interest in interpretation and a content of an interpretation report and determining matching. In the technique of JP2016-057695A, a determination of the presence or absence of the key image is not performed, and thus there may be a problem that the key image is not attached to the important findings in the interpretation report. Further, in the technique of JP2016-057695A, the key image and the finding sentence are not made to correspond to each other, and assigning the figure numbers or the like cannot be performed.

Further, JP6923863B discloses a technique of rearranging images in an order of finding sentences. However, the technique disclosed in JP6923863B is a technique in which a user makes an image correspond to findings, and does not reduce a burden on a doctor.

SUMMARY OF THE INVENTION

The present invention has been made in view of such circumstances, and an object thereof is to provide an information processing apparatus, an information processing method, and a program that reduce an error in making an image correspond to a sentence of a document including sentences and images and/or create a document that is easier to read as compared with an original document.

An information processing apparatus according to a first aspect of the present disclosure comprises an information processing apparatus including at least one processor, and at least one memory that stores a command to be executed by the at least one processor, in which the at least one processor is configured to acquire information regarding an object shown in one or more received images, acquire information described in one or more received sentences, determine presence or absence of correspondence between the image and the sentence based on the information regarding the object and the described information, and execute processing of assisting in creating a document including the image and the sentence based on the presence or absence of the correspondence.

According to the first aspect, it is possible to reduce the error in making the image correspond to the sentence of the document including the sentences and the images and/or to create the document that is easier to read as compared with the original document.

According to a second aspect of the present disclosure, in the information processing apparatus according to the first aspect, the processing may be processing of issuing a warning in a case where the image corresponding to the sentence is not present. Accordingly, it is possible to eliminate the omission of image attachment in which the image corresponding to the sentence is not present.

According to a third aspect of the present disclosure, in the information processing apparatus according to the first aspect or the second aspect, the processing may be processing of issuing a warning in a case where the image corresponding to the sentence is not present and a degree of importance of the sentence, which indicates a degree to which an image corresponding to the sentence is necessary, is equal to or larger than a threshold value. Accordingly, it is possible to eliminate the omission of image attachment in which there is no corresponding image even though the sentence is important.

According to a fourth aspect of the present disclosure, in the information processing apparatus according to any one of the first to third aspects, the processing may be processing of issuing a warning in a case where the sentence corresponding to the image is not present. Accordingly, it is possible to eliminate the omission of sentence description in which the sentence corresponding to the image is not present.

According to a fifth aspect of the present disclosure, in the information processing apparatus according to any one of the first to fourth aspects, the processing may be processing of rearranging, based on an order of one of the sentences and the images determined to have the correspondence, an order of the other. Accordingly, it is possible to match the order of sentences with the order of images to make the document easy to read.

According to a sixth aspect of the present disclosure, in the information processing apparatus according to any one of the first to fifth aspects, the processing may be processing of rearranging an order of the images based on an order of the sentences. Accordingly, it is possible to match the order of sentences with the order of images.

According to a seventh aspect of the present disclosure, in the information processing apparatus according to any one of the first to sixth aspects, the processing may be processing of assigning a figure number to the image out of the sentence and the image, which are determined to have the correspondence. Accordingly, it is possible to assign the figure number to the image to make the document description rich.

According to an eighth aspect of the present disclosure, in the information processing apparatus of the seventh aspect, the processing of assigning the figure number may be processing of assigning a figure number in an order in which the object shown in the image appears in the corresponding sentence. Accordingly, it is possible to assign the figure number in the order of sentence appearance.

According to a ninth aspect of the present disclosure, in the information processing apparatus according to the eighth aspect, the processing may be processing of assigning a figure number assigned to the image to the sentence out of the sentence and the image, which are determined to have the correspondence. Accordingly, it is possible to assign the figure number to the sentence to make the document description rich.

According to a tenth aspect of the present disclosure, in the information processing apparatus according to the ninth aspect, the processing may be processing of assigning a figure number to a corresponding portion of the sentence. Accordingly, it is possible to make the document easy to read.

According to an eleventh aspect of the present disclosure, in the information processing apparatus according to any one of the first to tenth aspects, the at least one processor may be configured to execute the processing each time any one of an input of the image or an input of the sentence is received. Accordingly, it is possible to execute the processing at any time.

According to a twelfth aspect of the present disclosure, in the information processing apparatus according to any one of the first to eleventh aspects, there may be provided a first mode in which the processing is executed each time any one of the input of the image or the input of the sentence is received and a second mode in which the processing is executed after inputs of all the images and all the sentences are received. Accordingly, it is possible to execute the processing in any mode.

According to a thirteenth aspect of the present disclosure, in the information processing apparatus according to any one of the first to twelfth aspects, the at least one processor may be configured to acquire a degree of certainty indicating certainty of correspondence between the information regarding the object and the described information, and determine whether or not the image and the sentence correspond to each other based on the degree of certainty. Accordingly, it is possible to appropriately determine the presence or absence of the correspondence between the image and the sentence.

According to a fourteenth aspect of the present disclosure, in the information processing apparatus according to any one of the first to thirteenth aspects, the at least one processor may be configured to analyze the received image or an original image serving as a creation source of the received image to acquire the information regarding the object. Accordingly, it is possible to appropriately acquire the information regarding the object.

According to a fifteenth aspect of the present disclosure, in the information processing apparatus according to any one of the first to fourteenth aspects, the image may be a key image based on a medical image.

According to a sixteenth aspect of the present disclosure, in the information processing apparatus according to the fifteenth aspect, the object may include at least one of an organ or a tumor, and the information regarding the object includes at least one of a size, a property, a disease name, a position, or a feature amount.

An information processing method according to a seventeenth aspect of the present disclosure is an information processing method including, by at least one processor, acquiring information regarding an object shown in one or more received images, acquiring information described in one or more received sentences, determining presence or absence of correspondence between the image and the sentence based on the information regarding the object and the described information, and executing processing of assisting in creating a document including the image and the sentence based on the presence or absence of the correspondence.

According to the seventeenth aspect, it is possible to reduce the error in making the image correspond to the sentence of the document including the sentences and the images and/or to create the document that is easier to read as compared with the original document. In the seventeenth aspect, it is possible to appropriately combine matters similar to the matters specified in the second to sixteenth aspects.

A program according to an eighteenth aspect of the present disclosure is a program causing a computer to execute the information processing method according to the seventeenth aspect. A non-transitory computer-readable recording medium such as a compact disk-read only memory (CD-ROM) storing the program according to the eighteenth aspect is also included in the present disclosure.

According to the eighteenth aspect, it is possible to reduce the error in making the image correspond to the sentence of the document including the sentences and the images and/or to create the document that is easier to read as compared with the original document.

According to the aspects of the present invention, it is possible to reduce the error in making the image correspond to the sentence of the document including the sentences and the images and/or to create the document that is easier to read as compared with the original document.

DESCRIPTION OF THE PREFERRED EMBODIMENTS

Hereinafter, preferred embodiments of the present invention will be described with reference to the accompanying drawings. Here, an information processing system for medical will be described as an example of an information processing apparatus, an information processing method, and a program according to the embodiment of the present invention.

Information Processing System for Medical

The information processing system for medical according to the present embodiment acquires information regarding an object shown in a key image based on a medical image, acquires information described in a finding sentence, determines whether or not there is correspondence between the key image and the finding sentence based on the information regarding the object and the information described in the finding sentence, and executes assistance processing of assisting creation of an interpretation report including the finding sentence and the key image based on the presence or absence of the correspondence. With the information processing system for medical, it is possible to reduce an error in making the medical image correspond to the finding sentence of the interpretation report (an example of "document") and/or to create an interpretation report that is easier to read as compared with an original interpretation report.

Figure 1:
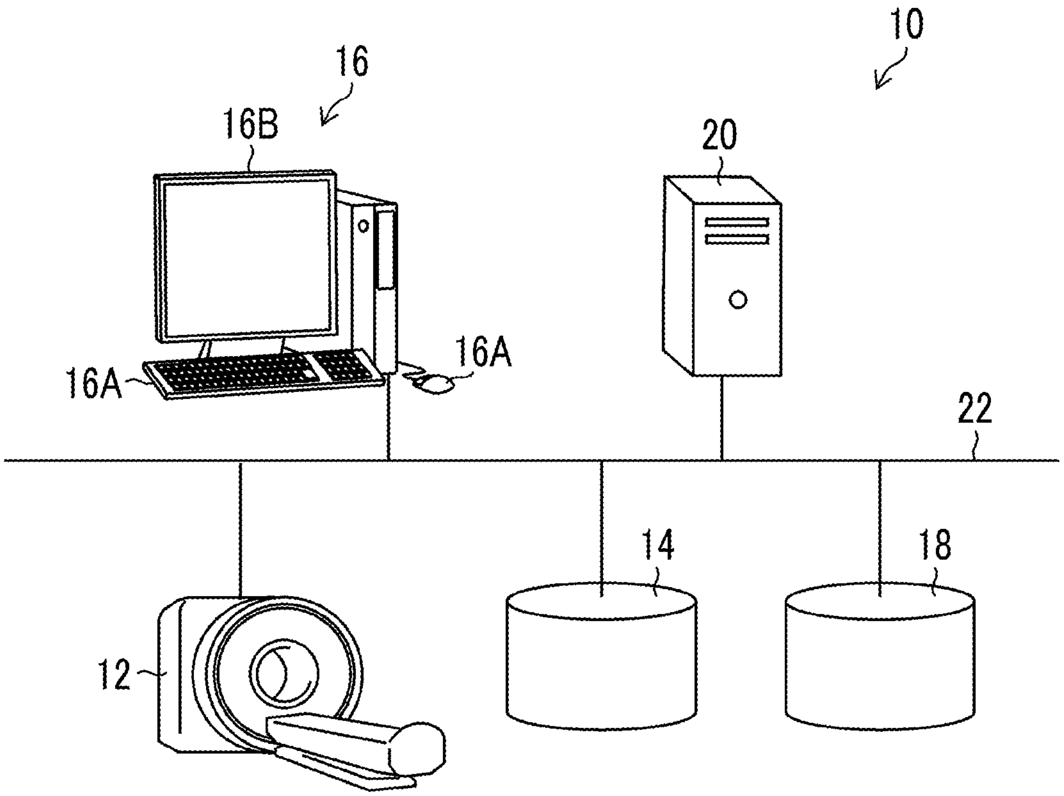
FIG. 1 is an entire configuration diagram of an information processing system for medical.

FIG. 1 is an entire configuration diagram of an information processing system for medical 10. As shown in FIG. 1, the information processing system for medical 10 comprises a medical image examination device 12, a medical image database 14, a user terminal device 16, an interpretation report database 18, and an information processing apparatus for medical 20.

The medical image examination device 12, the medical image database 14, the user terminal device 16, the interpretation report database 18, and the information processing apparatus for medical 20 are connected via a network 22 to transmit and receive data to and from each other. The network 22 includes a wired or wireless local area network (LAN) for communication connection of various devices in a medical institution. The network 22 may include a wide area network (WAN) that connects LANs of a plurality of medical institutions.

The medical image examination device 12 is an imaging device that images an examination target part of a subject and generates a medical image. Examples of the medical image examination device 12 include an X-ray imaging device, a computed tomography (CT) device, a magnetic resonance imaging (MRI) device, a positron emission tomography (PET) device, an ultrasound device, a computed radiography (CR) device using a flat X-ray detector, and an endoscope device.

The medical image database 14 is a database for managing the medical image captured by the medical image examination device 12. As the medical image database 14, a computer including a large-capacity storage device for storing the medical image is applied. Software providing a function of a database management system is incorporated into the computer.

The medical image may be a plurality of tomographic images captured by the CT device, the MRI device, or the like, or may be a three-dimensional reconstructed image reconstructed by using the plurality of tomographic images. The medical image may be a cross-sectional image in any direction of the three-dimensional reconstructed image.

As a format of the medical image, a digital imaging and communications in medicine (DICOM) standard can be applied. The medical image may be added with accessory information (Dicom tag information) defined in a Dicom standard. The term "image" used in the present specification includes not only an image itself, such as a photograph, but also image data which is a signal representing an image.

The user terminal device 16 is a terminal device for a doctor, who is a user, to create and view the interpretation report, and includes viewer software for the doctor to view the medical image. As the user terminal device 16, for example, a personal computer is applied. The user terminal device 16 may be a workstation, or may be a tablet terminal. The user terminal device 16 comprises an input device 16A and a display 16B which is a display device. The input device 16A may include a mouse and a keyboard.

The doctor uses the input device 16A to input an instruction to display the medical image. The user terminal device 16 causes the display 16B to display the medical image in response to the instruction. The doctor creates the key image from the medical image displayed by using the input device 16A. Further, the doctor uses the input device 16A to input the finding sentence which is a sentence indicating an interpretation result of the medical image. In this manner, the doctor creates the interpretation report including the key image and the finding sentence by using the user terminal device 16.

The key image is an image that is determined to be important in the interpretation based on a content of the finding sentence, among the medical images captured in the examination of the subject which is a target of the interpretation report.

The interpretation report database 18 is a database that manages the interpretation report created by the doctor. As the interpretation report database 18, a computer provided with a large-capacity storage device for storing the interpretation report is applied. Software providing a function of a database management system is incorporated into the computer. The medical image database 14 and the interpretation report database 18 may be configured by one computer.

Figure 2:
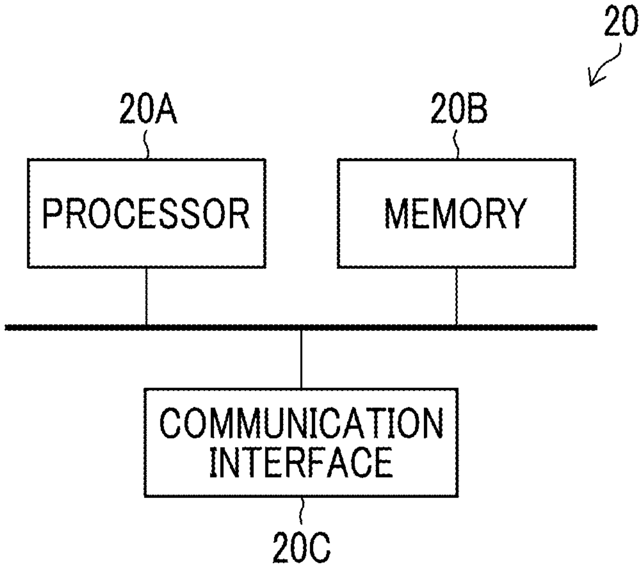
FIG. 2 is a block diagram showing an electric configuration of an information processing apparatus for medical.

The information processing apparatus for medical 20 is an apparatus that executes assistance processing which is processing of assisting the creation of interpretation report. As the information processing apparatus for medical 20, a personal computer or a workstation (an example of "computer") can be applied. FIG. 2 is a block diagram showing an electric configuration of the information processing apparatus for medical 20. As shown in FIG. 2, the information processing apparatus for medical 20 comprises a processor 20A, a memory 20B, and a communication interface 20C.

The processor 20A executes a command stored in the memory 20B. A hardware structure of the processor 20A is various processors as shown below. Various processors include a central processing unit (CPU) as a general-purpose processor that acts as various function units by executing software (program), a graphics processing unit (GPU) as a processor specialized in image processing, a programmable logic device (PLD) as a processor of which a circuit configuration can be changed after manufacture, such as a field programmable gate array (FPGA), a dedicated electric circuit as a processor which has a circuit configuration specifically designed to execute specific processing, such as an application specific integrated circuit (ASIC), and the like.

One processing unit may be configured by using one of these various processors, or may be configured by using two or more processors of the same type or different types (for example, a plurality of FPGAs, or a combination of a CPU and an FPGA, or a combination of a CPU and a GPU). Further, a plurality of function units may be configured by using one processor. As an example of configuring the plurality of function units with one processor, first, as represented by a computer such as a client or a server, a form of configuring one processor with a combination of one or more CPUs and software and causing the processor to act as the plurality of function units is present. A second example of the configuration is an aspect in which a processor that realizes functions of an entire system including the plurality of function units with one integrated circuit (IC) chip is used, as typified by a system-on-chip (SoC). As described above, various function units are composed of using one or more of the various processors described above as a hardware structure.

Further, the hardware structure of these various processors is, more specifically, an electric circuit (circuitry) combining circuit elements such as a semiconductor element.

The memory 20B stores a command to be executed by the processor 20A. The memory 20B includes a random access memory (RAM) and a read only memory (ROM) (not shown). The processor 20A uses the RAM as a work area, executes software using various parameters and programs including an information processing program for medical described below, which are stored in the ROM, and executes various kinds of processing of the information processing apparatus for medical 20 by using the parameters stored in the ROM or the like.

The communication interface 20C controls, according to a predetermined protocol, communication with the medical image examination device 12, the medical image database 14, the user terminal device 16, and the interpretation report database 18 via the network 22.

The information processing apparatus for medical 20 may be a cloud server that can be accessed from a plurality of medical institutions via the Internet. The processing performed in the information processing apparatus for medical 20 may be a usage-based billing or fixed-fee cloud service.

Functional Configuration of Information Processing Apparatus for Medical

Figure 3:
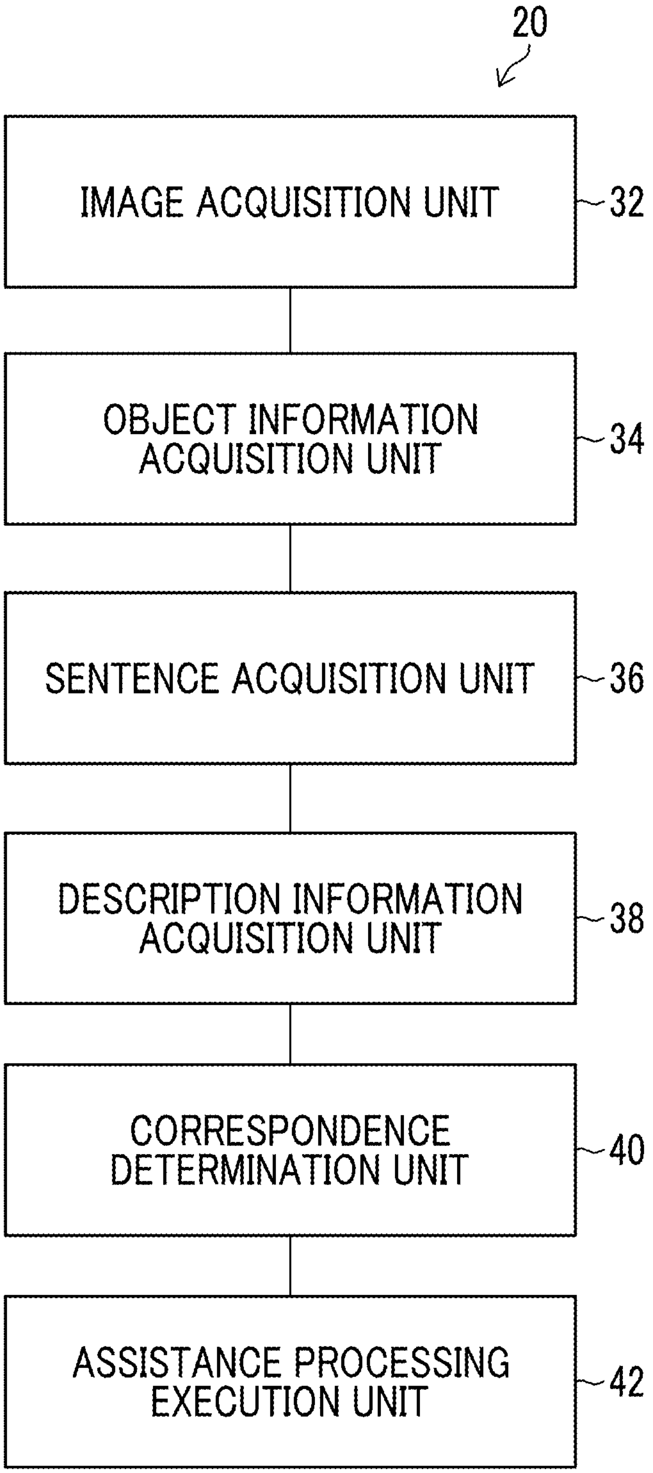
FIG. 3 is a block diagram showing a functional configuration of the information processing apparatus for medical.

FIG. 3 is a block diagram showing a functional configuration of the information processing apparatus for medical 20. Each function of the information processing apparatus for medical 20 is realized by the processor 20A executing the information processing program for medical, which is stored in the memory 20B. As shown in FIG. 3, the information processing apparatus for medical 20 comprises an image acquisition unit 32, an object information acquisition unit 34, a sentence acquisition unit 36, a description information acquisition unit 38, a correspondence determination unit 40, and an assistance processing execution unit 42.

The image acquisition unit 32 acquires one or more key images used in the interpretation report. For example, the image acquisition unit 32 acquires the medical image from the medical image database 14 and displays the medical image on the display 16B. The doctor creates the key image by trimming a region, which is determined to be important in the interpretation, from the medical image displayed on the display 16B by using the input device 16A. The image acquisition unit 32 receives the key image created by the doctor. The image acquisition unit 32 may acquire the key image that has already been described in the interpretation report.

The object information acquisition unit 34 acquires object information regarding an object shown in one or more key images, which are acquired by the image acquisition unit 32. The object information acquisition unit 34 may analyze the key image to acquire the object information, or may analyze the medical image, which is an original image serving as a creation source of the key image, to acquire the object information. The object includes at least one of an organ or a tumor. The object information includes at least one of a size, a property, a disease name, a position, or a feature amount. The object information acquisition unit 34 may acquire, as the object information, an image feature indicating the feature amount of the key image. The image feature may be expressed by an image feature vector obtained by converting the key image into a feature vector, or may be a feature map of a plurality of channels.

The sentence acquisition unit 36 acquires one or more finding sentences used in the interpretation report. For example, the doctor uses the input device 16A to input the finding sentence related to the key image. The sentence acquisition unit 36 receives the finding sentence input by the doctor. The sentence acquisition unit 36 may receive structured data obtained by structuring the finding sentence input by the doctor using structure analysis.

The description information acquisition unit 38 acquires description information described in one or more finding sentences, which are acquired by the sentence acquisition unit 36. The description information acquisition unit 38 may acquire, as the description information, a language feature vector from which the feature amount corresponding to the finding sentence is extracted.

The correspondence determination unit 40 determines whether or not there is correspondence for each combination of the key image acquired by the image acquisition unit 32 and the finding sentence acquired by the sentence acquisition unit 36, based on the object information acquired by the object information acquisition unit 34 and the description information acquired by the description information acquisition unit 38. The correspondence determination unit 40 may acquire a degree of certainty indicating certainty that the object information corresponds to the description information to determine whether or not there is correspondence between the key image and the finding sentence based on the acquired degree of certainty. For example, in a case where the degree of certainty between the object information of the key image and the description information of the finding sentence is equal to or larger than a threshold value, the correspondence determination unit 40 may determine that there is the correspondence between the key image and the finding sentence. In a case where the degree of certainty therebetween is less than the threshold value, the correspondence determination unit 40 may determine that there is no correspondence between the key image and the finding sentence.

The assistance processing execution unit 42 executes the assistance processing based on the presence or absence of the correspondence determined by the correspondence determination unit 40. The assistance processing may be processing of issuing a warning in a case where the key image corresponding to the finding sentence is not present. The assistance processing may be processing of issuing the warning in a case where the key image corresponding to the finding sentence is not present and the finding sentence is important findings. In a case where the key image corresponding to the finding sentence is not present and the finding sentence is not the important findings, the assistance processing may not be performed.

The important findings are findings for which the key image needs to be created. The findings for which the key image needs to be created are, for example, findings in which a specific disease is described. The assistance processing execution unit 42 may calculate a degree of importance of the finding sentence, which indicates a degree to which a key image corresponding to the finding sentence is necessary, to determine that there is the important findings in a case where the degree of importance of the finding sentence is equal to or larger than a threshold value.

The assistance processing may be processing of issuing the warning in a case where the finding sentence corresponding to the key image is not present. The assistance processing may be processing of rearranging, based on an order of one of the finding sentence and the key image, which are determined to have the correspondence, an order of the other thereof. The assistance processing may be processing of rearranging the order of key images based on the order of finding sentences.

The assistance processing may be processing of assigning a figure number to the key image out of the finding sentence and the key image, which are determined to have the correspondence. The processing of assigning the figure numbers may be processing of assigning the figure number in an order in which the object shown in the key image appears in the corresponding finding sentence.

The assistance processing may be processing of assigning the figure number assigned to the key image to the finding sentence out of the finding sentence and the key image, which are determined to have the correspondence. The assistance processing may be processing of assigning the figure number to a corresponding portion of the finding sentence.

The assistance processing execution unit 42 may execute the assistance processing each time any one of the key image in the image acquisition unit 32 or the finding sentence in the sentence acquisition unit 36 is received. The assistance processing execution unit 42 may execute the assistance processing after all the key images in the image acquisition unit 32 and all the finding sentences in the sentence acquisition unit 36 are received. The information processing apparatus for medical 20 may be provided with a first mode in which the assistance processing is executed each time any one of the key image or the finding sentence is received, and a second mode in which the assistance processing is executed after the acquisition of all the key images and all the finding sentences is received. The first mode and the second mode may be switchable by the operation of the input device 16A by the doctor.

Information Processing Method for Medical

Figure 4:
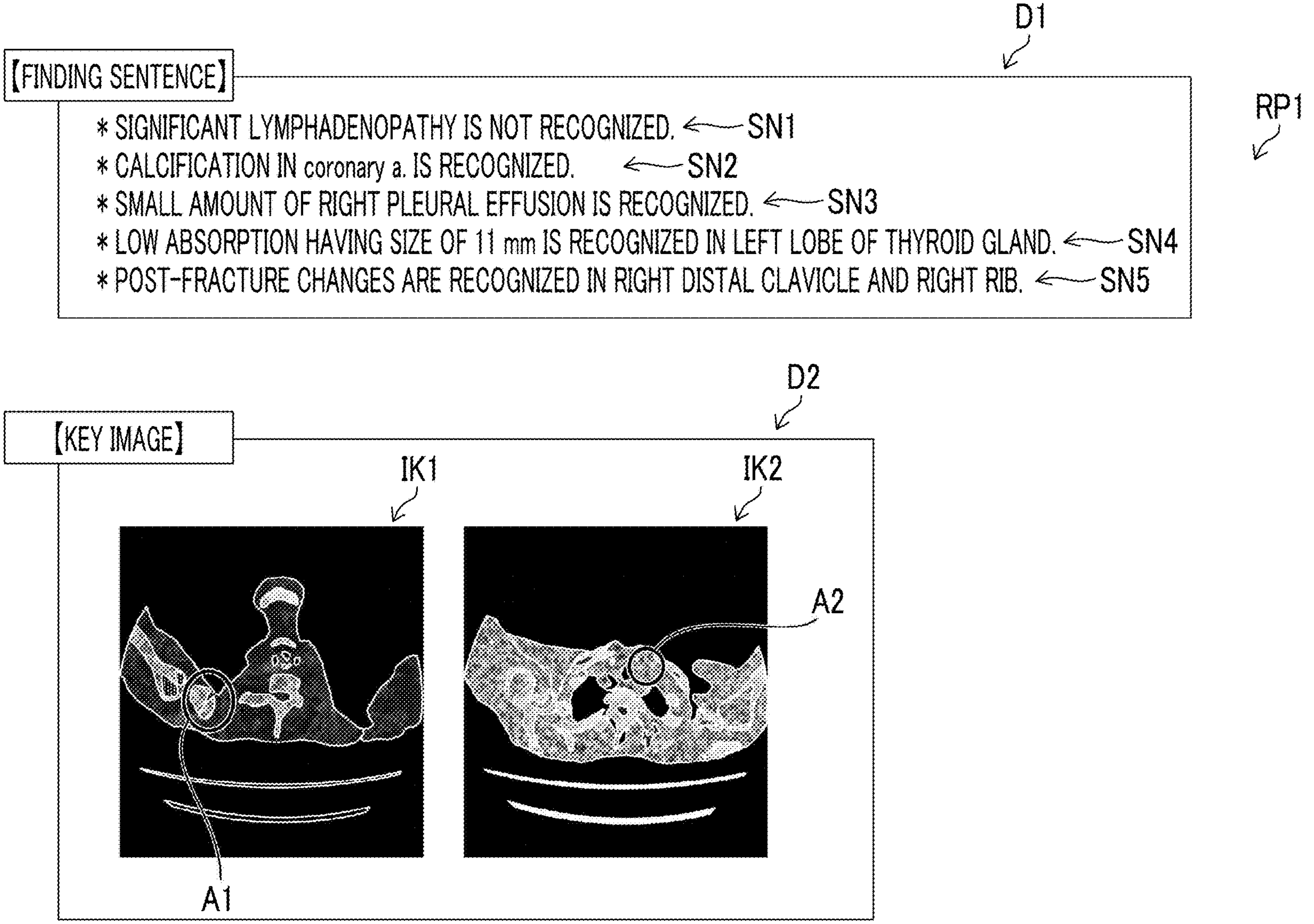
FIG. 4 is a diagram showing an interpretation report.

FIG. 4 is a diagram showing an interpretation report RP1 displayed on the display 16B of the user terminal device 16. The interpretation report RP1 is created by the doctor.

A display region D1 of the interpretation report RP1 is a region in which the finding sentence is displayed. In the display region D1, a finding sentence SN1 "Significant lymphadenopathy is not recognized.", a finding sentence SN2 "Calcification in coronary a. is recognized.", a finding sentence SN3 "Small amount of right pleural effusion is recognized.", a finding sentence SN4 "Low absorption having size of 11 mm is recognized in left lobe of thyroid gland.", and a finding sentence SN5 "Post-fracture changes are recognized in right distal clavicle and right rib." are displayed in order from the top.

Further, a display region D2 of the interpretation report RP1 is a region in which the key image is displayed. In the display region D2, a key image IK1 including a lesion region A1 and a key image IK2 including a lesion region A2 are displayed in order from the left.

Figure 5:
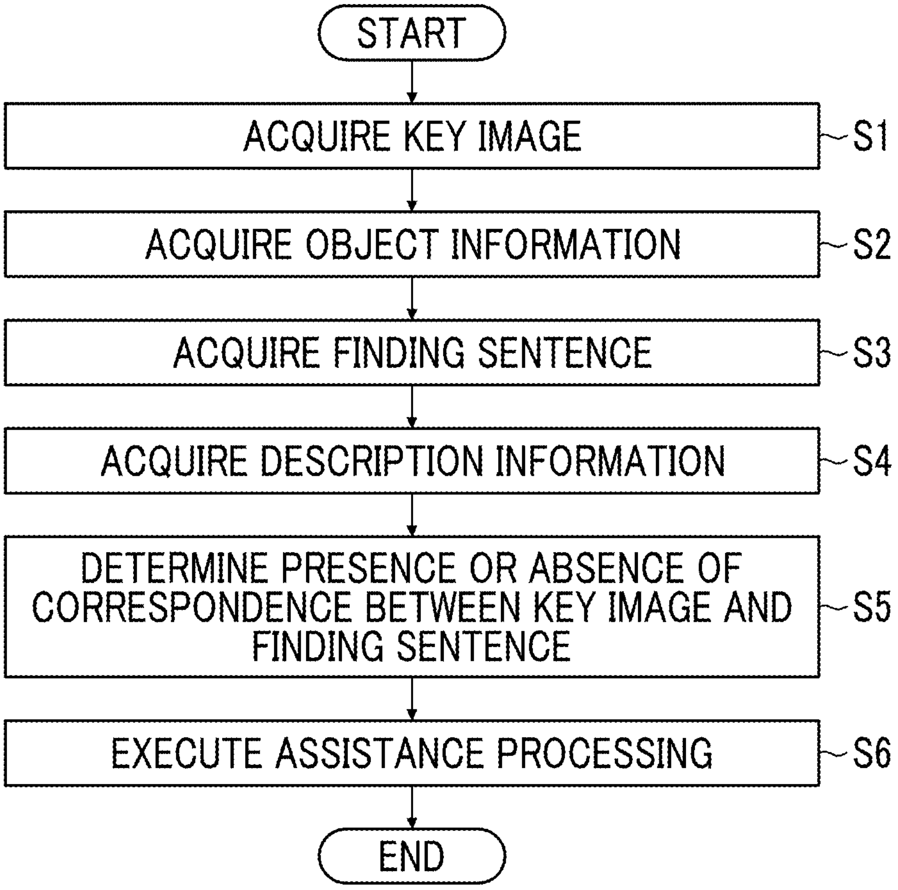
FIG. 5 is a flowchart showing an information processing method for medical.

FIG. 5 is a flowchart showing an information processing method for medical using the information processing apparatus for medical 20. The information processing method for medical is a method of executing, based on the object information shown in the key image and the description information described in the finding sentence, the assistance processing based on the presence or absence of the correspondence between the key image and the finding sentence. The information processing method for medical is realized by the processor 20A executing the information processing program for medical, which is stored in the memory 20B. The information processing program for medical may be provided to the information processing apparatus for medical 20 by a computer-readable non-transitory storage medium, or may be provided to the information processing apparatus for medical 20 via the Internet. Here, an example will be described in which the assistance processing is executed on the interpretation report RP1 shown in FIG. 4.

In step S1, the image acquisition unit 32 acquires one or more key images used in the interpretation report. Here, the image acquisition unit 32 acquires the key image IK1 and the key image IK2.

In step S2, the object information acquisition unit 34 acquires the object information regarding the object shown in each of the key image IK1 and the key image IK2, which are acquired in step S1. Here, the object information acquisition unit 34 acquires, as the object information, information on the lesion region A1 from the key image IK1 and information on the lesion region A2 from the key image IK2.

In step S3, the sentence acquisition unit 36 acquires one or more finding sentences used in the interpretation report. Here, the sentence acquisition unit 36 acquires the finding sentences SN1 to SN5.

In step S4, the description information acquisition unit 38 acquires the description information described in each of the finding sentences SN1 to SN5, which are acquired in step S3. Here, the description information acquisition unit 38 acquires, as the description information, "not recognized" from the finding sentence SN1, "coronary a." and "calcification" from the finding sentence SN2, "small amount" and "right pleural effusion" from the finding sentence SN3, "left lobe of thyroid gland" and "low absorption having size of 11 mm" from the finding sentence SN4, and "right distal clavicle", "right rib", and "post-fracture change" from the finding sentence SN5.

In step S5, the correspondence determination unit 40 determines the presence or absence of the correspondence between the key images IK1 and IK2 and the finding sentences SN1 to SN5 in a round-robin manner, based on the object information acquired in step S2 and the description information acquired in step S4. That is, the correspondence determination unit 40 determines the presence or absence of the correspondence in respective combinations of the key image IK1 and the finding sentence SN1, the key image IK1 and the finding sentence SN2, . . . , the key image IK1 and the finding sentence SN5, the key image IK2 and the finding sentence SN1, the key image IK2 and the finding sentence SN2, . . . , the key image IK2 and the finding sentence SN5. Here, the correspondence determination unit 40 is assumed to determine that there is the correspondence in the combination of the key image IK1 and the finding sentence SN5 and in the combination of the key image IK2 and the finding sentence SN4.

In step S6, the assistance processing execution unit 42 executes the assistance processing based on the presence or absence of the correspondence determined in step S5. Here, the assistance processing is assumed to be processing of rearranging the order of key images based on the order of finding sentences in a plurality of combinations of the finding sentences and the key images, which are determined to have the correspondence.

Figure 6:
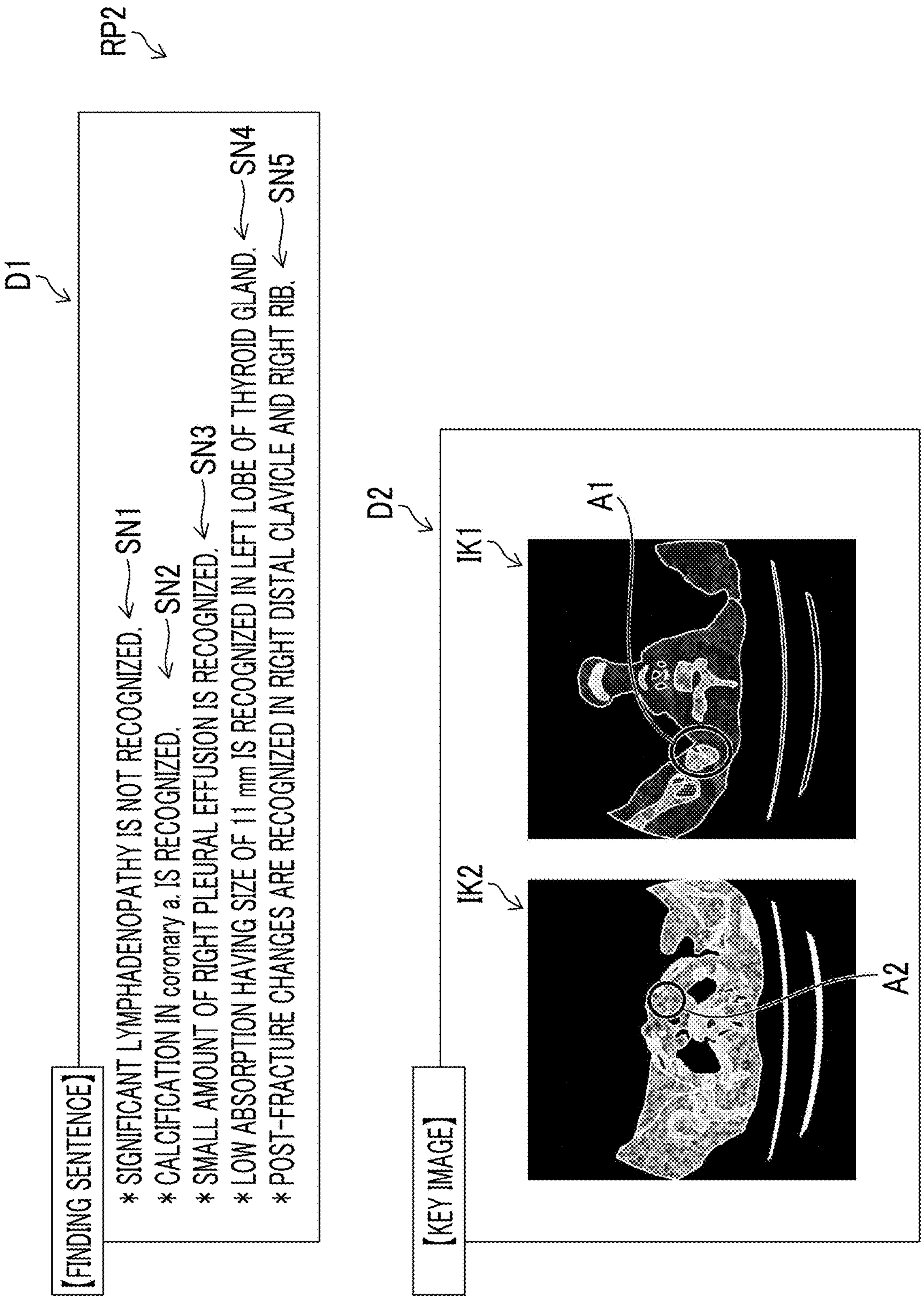
FIG. 6 is a diagram showing an example of the interpretation report.

FIG. 6 is a diagram showing an interpretation report RP2 displayed on the display 16B of the user terminal device 16. The interpretation report RP2 is obtained as a result of execution of the assistance processing on the interpretation report RP1. In the interpretation report RP2, the display of the finding sentences SN1 to SN5 in the display region D1 is the same as in the interpretation report RP1. Further, in the interpretation report RP2, a position of the key image in the display region D2 is changed from the position thereof in the interpretation report RP1, and the key image IK2 and the key image IK1 are displayed in order from the left.

That is, in the combination of the key image IK1 and the finding sentence SN5 and the combination of the key image IK2 and the finding sentence SN4, which are determined to have the correspondence, the assistance processing execution unit 42 disposes the key image IK2 corresponding to the finding sentence SN4, out of the finding sentence SN5 and the finding sentence SN4, that is higher in order from the top in the display region D1 on a left side and the key image IK1 corresponding to the finding sentence SN5 that is lower in order from the top on a right side.

It is considered that the finding sentences of the interpretation report are read in order from top to bottom, and the key images are visually recognized in order from left to right. Therefore, with rearrangement of the left-right order of the key images based on the top-bottom order of the finding sentences, it is possible to create the interpretation report that is easy to read.

Figure 7:
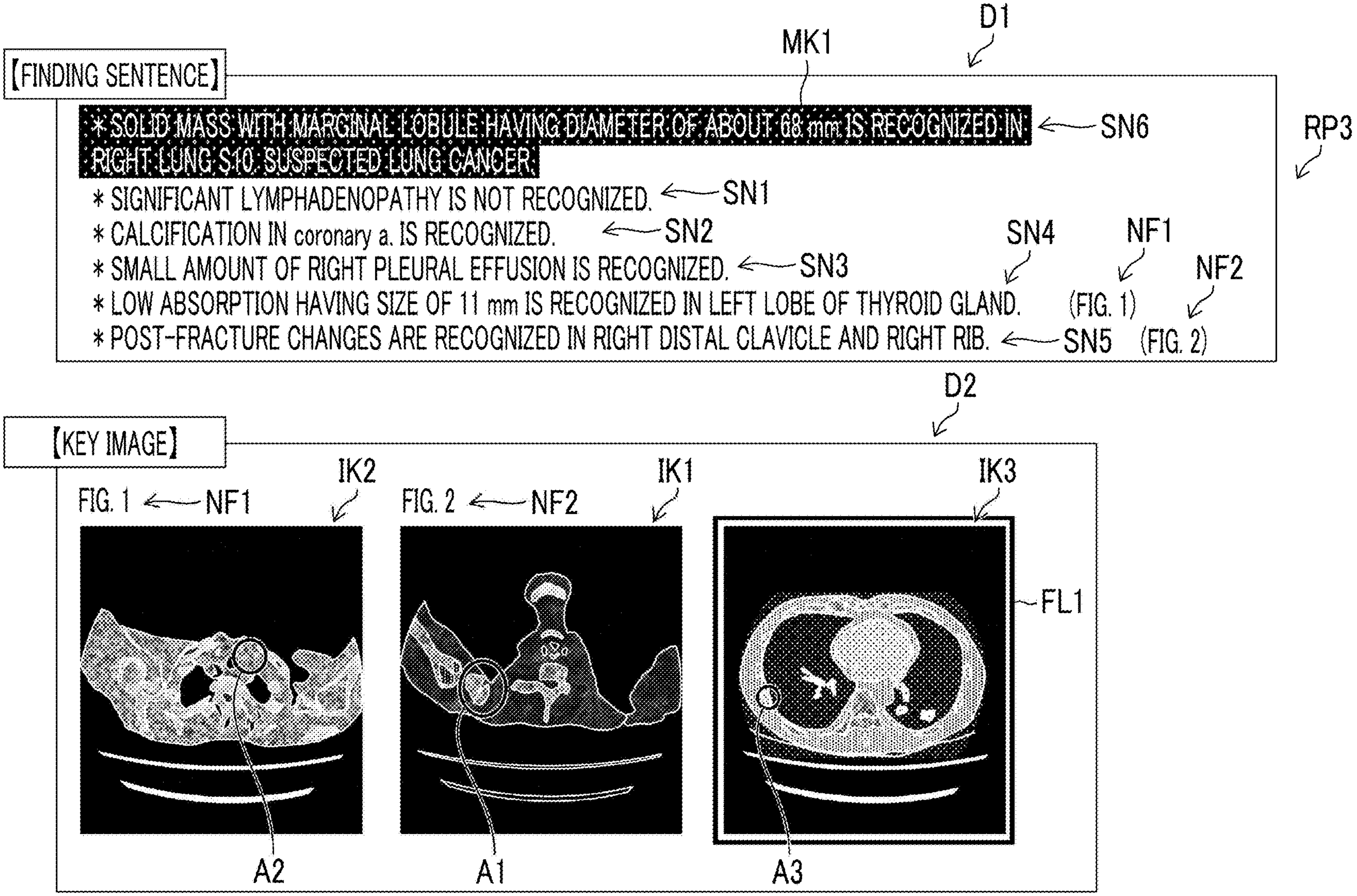
FIG. 7 is a diagram showing an example of the interpretation report.

The assistance processing is not limited to the processing of rearranging the order of the key images. FIG. 7 is a diagram showing an interpretation report RP3 displayed on the display 16B of the user terminal device 16. An interpretation report RP3 is obtained as a result of the execution of the assistance processing on the interpretation report RP1. Here, a case is shown in which a finding sentence SN6 "Solid mass with marginal lobule having diameter of about 68 mm is recognized in right lung S10. Suspected lung cancer." and a key image IK3 including a lesion region A3 are described, in addition to the finding sentences SN1 to SN5 and the key images IK1 and IK2 as in FIG. 6.

In the interpretation report RP3, a marker MK1 that highlights the finding sentence SN6 warns that the key image corresponding to the finding sentence SN6 is not present (an example of "non-presence"). The finding sentence SN6 may be warned only in a case where the corresponding key image is not present and the finding sentence SN6 is the important findings. Here, since the description information "solid mass" of the finding sentence SN6 is the description of a disease, the finding sentence SN6 is determined to be the important findings.

Further, in the display region D2 of the interpretation report RP3, as in the interpretation report RP2, the key image IK2 and the key image IK1 are displayed in order from the left based on the order of the corresponding finding sentences SN4 and SN5. Furthermore, the figure numbers are assigned to the key image IK2 and the key image IK1 in order from the left. Here, "FIG. 1" is assigned as a figure number NF1 to the key image IK2, and "FIG. 2" is assigned as a figure number NF2 to the key image IK1. As described above, the figure number NF1 and the figure number NF2 are assigned in an order in which the lesion region A2 shown in the key image IK2 and the lesion region A1 shown in the key image IK1 appear in the corresponding finding sentence SN4 and finding sentence SN5, respectively.

The finding sentence SN4 and the finding sentence SN5 are assigned with the figure number NF1 and the figure number NF2 of the corresponding key images, respectively. The figure number NF1 and the figure number NF2 which are assigned to the finding sentence SN4 and the finding sentence SN5 may be assigned to corresponding portions of the finding sentence SN4 and the finding sentence SN5.

In the interpretation report RP3, a frame FL1 that highlights the key image IK3 warns that the finding sentence corresponding to the key image IK3 is not present.

Details of Making Key Image Correspond to Finding Sentence

Figure 8:
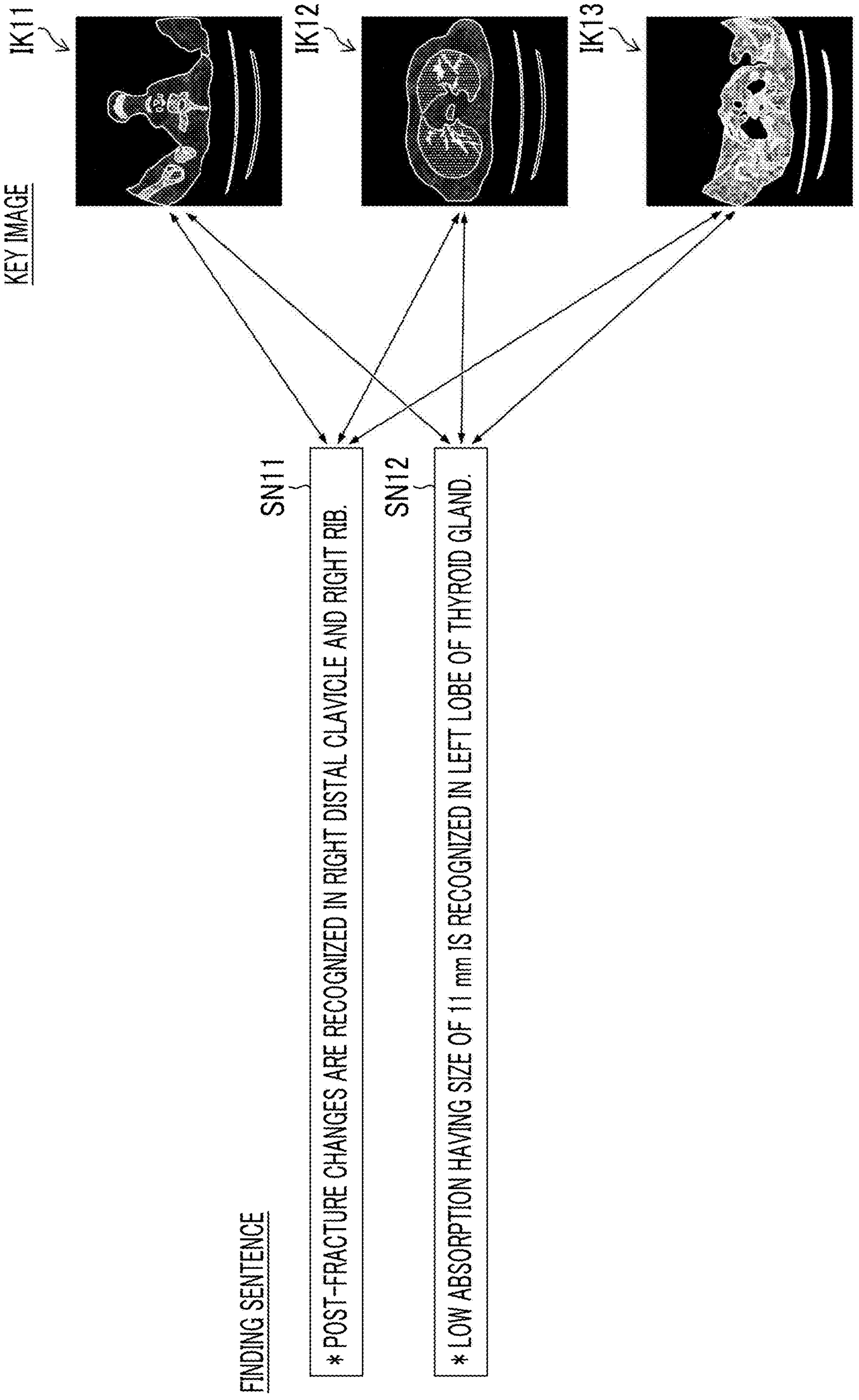
FIG. 8 is a diagram for describing correspondence between a finding sentence and a key image using a degree of certainty.

FIG. 8 is a diagram for describing making the finding sentence correspond to the key image using the degree of certainty. In the example shown in FIG. 8, the image acquisition unit 32 acquires the key image IK11, the key image IK12, and the key image IK13, and the sentence acquisition unit 36 acquires a finding sentence SN11 "Post-fracture changes are recognized in right distal clavicle and right rib." and a finding sentence SN12 "Low absorption having size of 11 mm is recognized in left lobe of thyroid gland". In this case, the correspondence determination unit 40 calculates the degree of certainty, based on the object information and the description information, for each combination of the finding sentence SN11 and the key image IK11, the finding sentence SN11 and the key image IK12, the finding sentence SN11 and the key image IK13, the finding sentence SN12 and the key image IK11, the finding sentence SN12 and the key image IK12, and the finding sentence SN12 and the key image IK13 to determine the presence or absence of the correspondence.

The degree of certainty is an index indicating that the certainty of the correspondence between the object information and the description information is higher as a value of the degree of certainty is larger, and is, for example, a value of zero or more and one or less. Further, the threshold value is, for example, 0.90. That is, in a case where the degree of certainty is 0.90 or more, the correspondence determination unit 40 determines that there is the correspondence between the key image and the finding sentence, and makes the key image correspond to the finding sentence.

Figure 9:
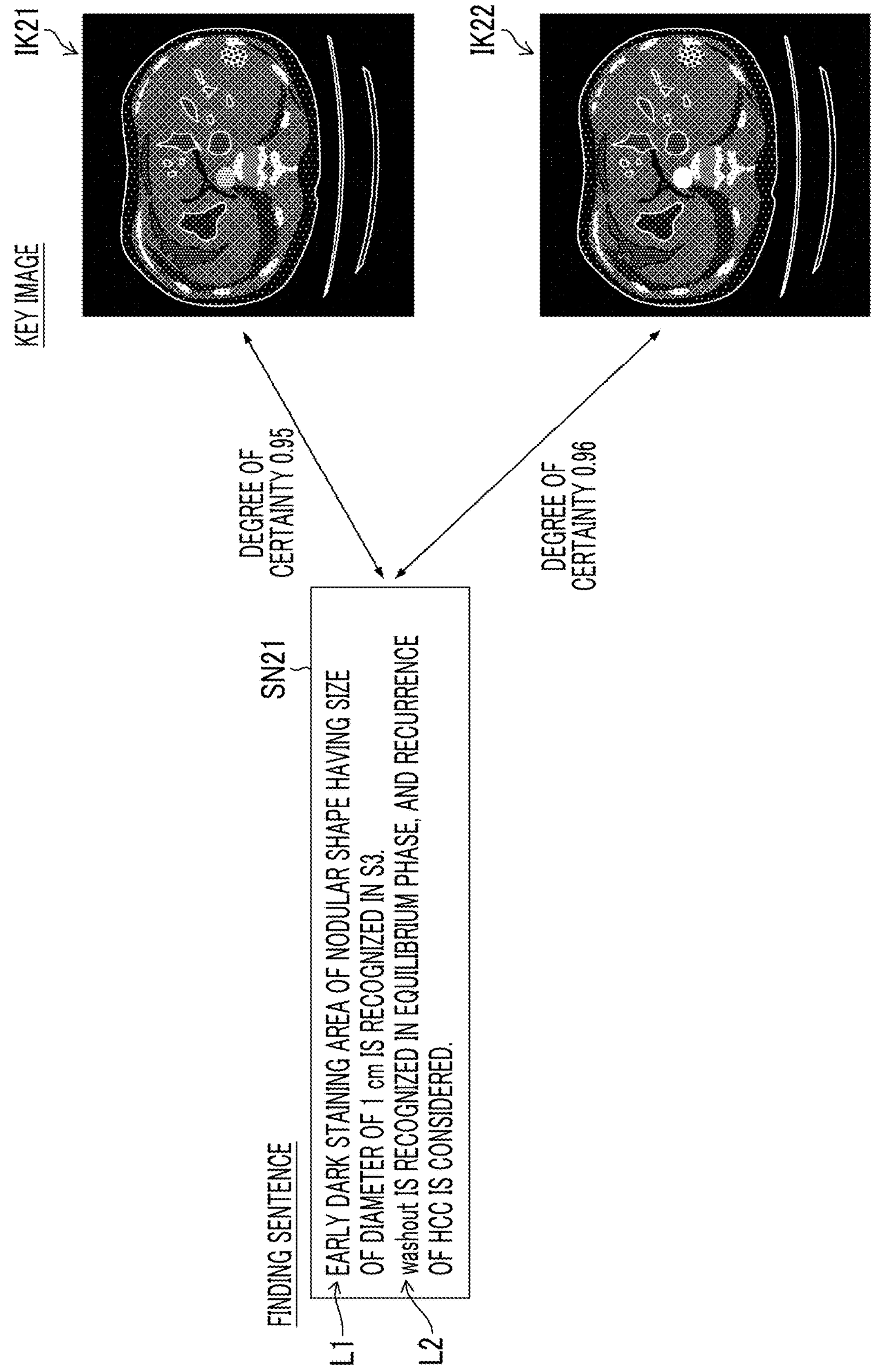
FIG. 9 is a diagram for describing a case where two or more key images correspond to one finding sentence.

FIG. 9 is a diagram for describing a case where two or more key images and one finding sentence are in correspondence with each other. In the example shown in FIG. 9, the degree of certainty between a finding sentence SN21 "Early dark staining area of nodular shape having size of diameter of 1 cm is recognized in S3. washout is recognized in equilibrium phase, and recurrence of HCC is considered." and a key image IK21 is 0.95. The degree of certainty between the finding sentence SN21 and a key image IK22 is 0.96. The key image IK21 and the key image IK22 are images at the same anatomical position, and both the key image IK21 and the key image IK22 have the degree of certainty higher than the threshold value of 0.90. Therefore, both the key image IK21 and the key image IK22 are in correspondence with the finding sentence SN21. As described above, two or more key images may correspond to one finding sentence.

The finding sentence SN21 includes a sentence L1 "Early dark staining area of nodular shape having size of diameter of 1 cm is recognized in S3." and a sentence L2 "washout is recognized in equilibrium phase, and recurrence of HCC is considered". However, the sentence L1 and the sentence L2 may be treated as different finding sentences.

Figure 10:
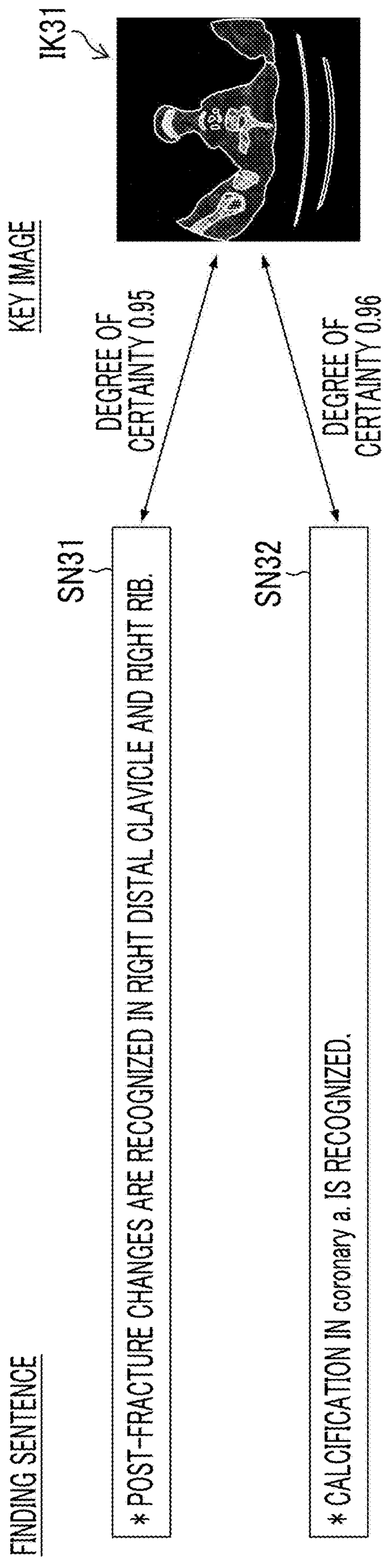
FIG. 10 is a diagram for describing a case where one key image corresponds to a plurality of finding sentences.

FIG. 10 is a diagram for describing a case where the degree of certainty between one key image and a plurality of finding sentences is equal to or larger than the threshold value. In the example shown in FIG. 10, the degree of certainty between a finding sentence SN31 "Post-fracture changes are recognized in right distal clavicle and right rib." and a key image IK31 is 0.95, which is equal to or larger than the threshold value 0.90. Further, the degree of certainty between a finding sentence SN32 "Calcification in coronary a. is recognized." and the key image IK31 is 0.90, which is equal to or larger than the threshold value 0.90. In this case, the key image IK31 is made to correspond to the finding sentence having a relatively high degree of certainty. That is, the correspondence determination unit 40 makes the key image IK31 correspond to the finding sentence SN31. As described above, one finding sentence corresponds to one key image.

Language Feature Extraction Model

The description information acquisition unit 38 may comprise a language feature extraction model. The language feature extraction model is a learned model trained to receive an input of a finding sentence and output a corresponding finding feature.

Example of Data Used for Machine Learning

Figure 11:
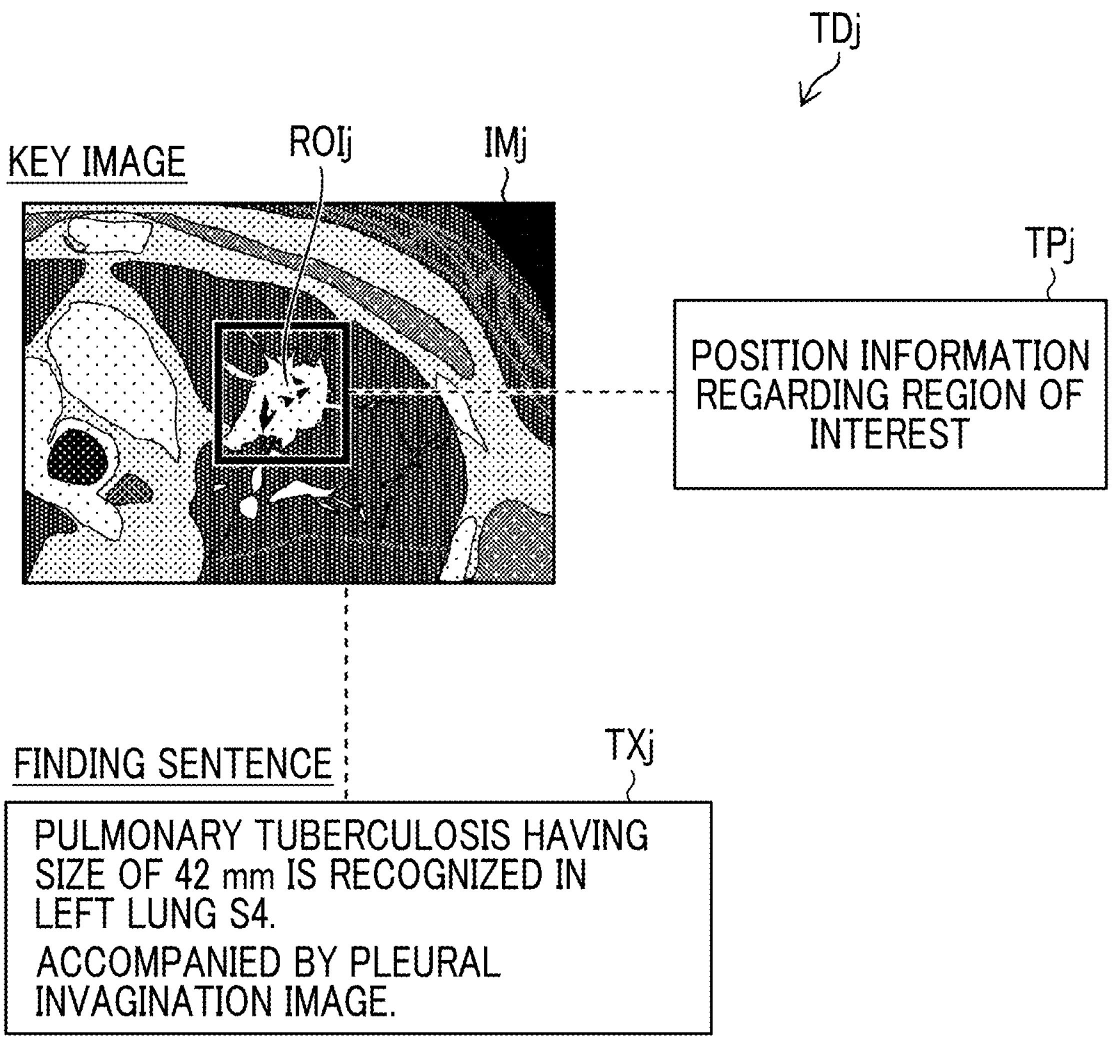
FIG. 11 is an explanatory diagram showing an example of data for learning used in a method of generating a language feature extraction model.

FIG. 11 is an explanatory diagram showing an example of data for learning (training) used in a method of generating the language feature extraction model. Here, an example of training data TDj including a key image IMj, position information TPj regarding a region of interest ROIj in the key image IMj, and a finding sentence TXj describing the region of interest ROIj will be described. The key image IMj, the position information TPj regarding the region of interest ROIj, and the finding sentence TXj are associated with each other. The subscript j represents an index number as an identification reference numeral of an associated data set. The region of interest ROIj is mainly a lesion region.

The position information TPj regarding the region of interest ROIj is information that may specify a position of the region of interest ROIj in the key image IMj. The position information TPj may be coordinate information indicating coordinates in the key image IMj, may be information indicating a region or a range in the key image IMj, or may be a combination of these pieces of information. The position information TPj may be information assigned as annotation information for the key image IMj, or may be meta information attached to the key image IMj, such as a DICOM tag.

The finding sentence TXj may be, for example, a sentence described in the interpretation report. Here, as the finding sentence TXj, a text which is unstructured data in a free description type sentence format before being structured is illustrated, but structured data structured by structure analysis of a sentence may be also used.

Such training data TDj can be generated by sampling appropriate data from a database in which pieces of data of medical images and interpretation reports related to past examination cases in a medical institution such as a hospital are accumulated and stored in an associated manner.

Configuration Example of Machine Learning Device

Figure 12:
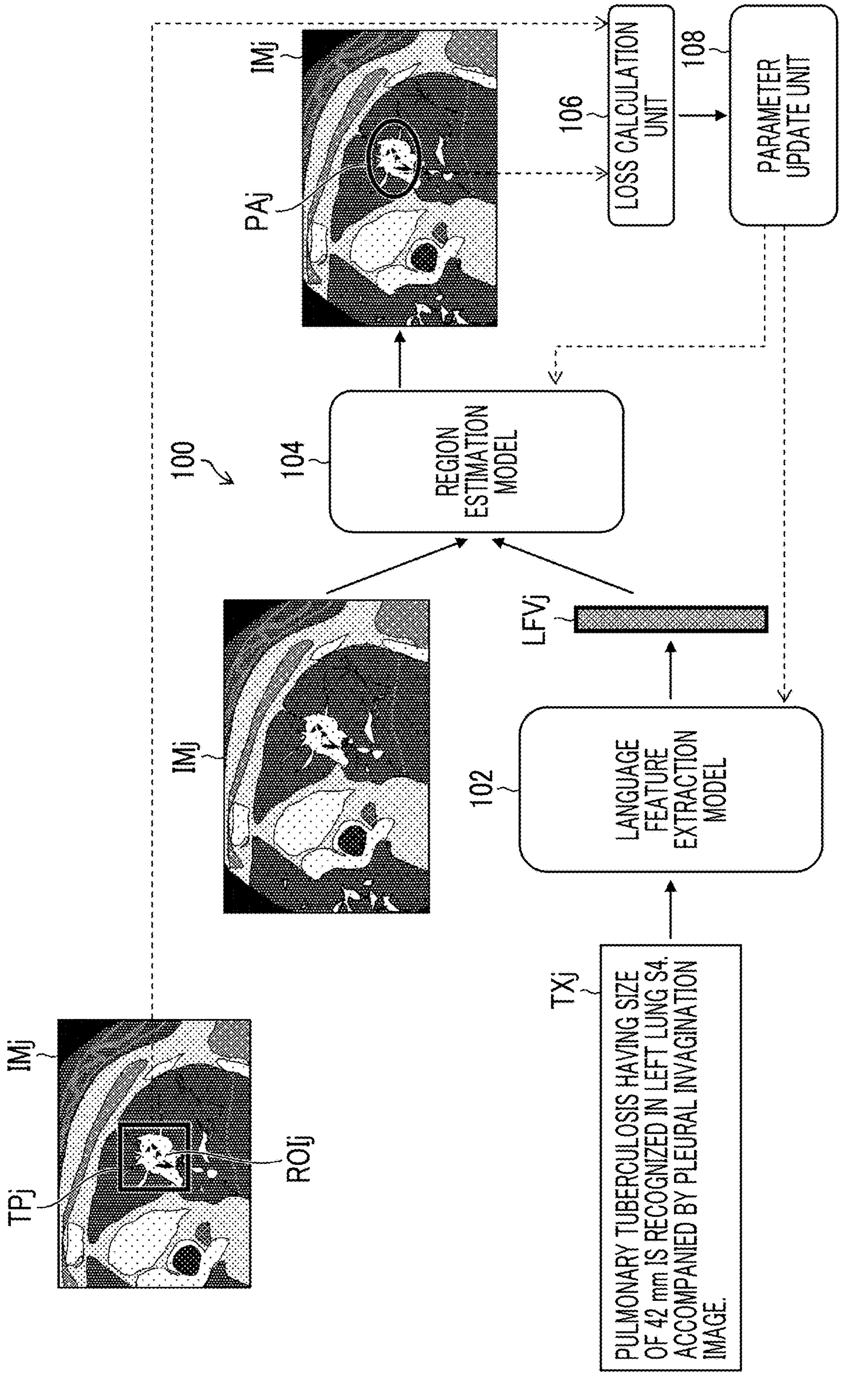
FIG. 12 is a block diagram schematically showing a functional configuration of a machine learning device that causes the language feature extraction model to learn.

FIG. 12 is a block diagram schematically showing a functional configuration of a machine learning device 100 that causes the language feature extraction model to learn. The machine learning device 100 may be the same device as the information processing apparatus for medical 20 or may be a device different from the information processing apparatus for medical 20.

The machine learning device 100 includes a language feature extraction model 102, a region estimation model 104, a loss calculation unit 106, and a parameter update unit 108. A function of each unit of the machine learning device 100 may be realized by a combination of hardware and software of a computer.

As the language feature extraction model 102, for example, a natural language processing model called bidirectional encoder representations from transformers (BERT) is applied. The language feature extraction model 102 receives an input of the finding sentence TXj which is a text, extracts the feature amount corresponding to the input finding sentence TXj, and outputs a finding feature LFVj which is the language feature vector (finding feature vector).

As the region estimation model 104, for example, a convolutional neural network (CNN) is applied. The region estimation model 104 receives inputs of the key image IMj and the finding feature LFVj, estimates the lesion region in the key image IMj referred to in the input finding sentence TXj, and outputs estimated region information PAj indicating a position of the estimated lesion region. The estimated region information PAj may be, for example, coordinate information that specifies a position of a rectangle (bounding box) surrounding a range of the estimated lesion region, or a segmentation mask image that specifies the estimated lesion region in a pixel unit.

The loss calculation unit 106 calculates a loss indicating an error between the estimated lesion region indicated by the estimated region information PAj output from the region estimation model 104 and the region of interest ROIj of a correct answer indicated by the position information TPj of a correct answer associated with the key image IMj.

The parameter update unit 108 calculates, based on the loss calculated by the loss calculation unit 106, an update amount of a parameter of each model of the region estimation model 104 and the language feature extraction model 102 such that the loss becomes small and updates the parameter of each model according to the calculated update amount. The parameter of each model includes a filter coefficient (weight for coupling between nodes) of a filter used for processing each layer of a neural network, a node bias, and the like. The parameter update unit 108 optimizes the parameter of each model by, for example, a method such as a stochastic gradient descent (SGD) method.

Figure 13:
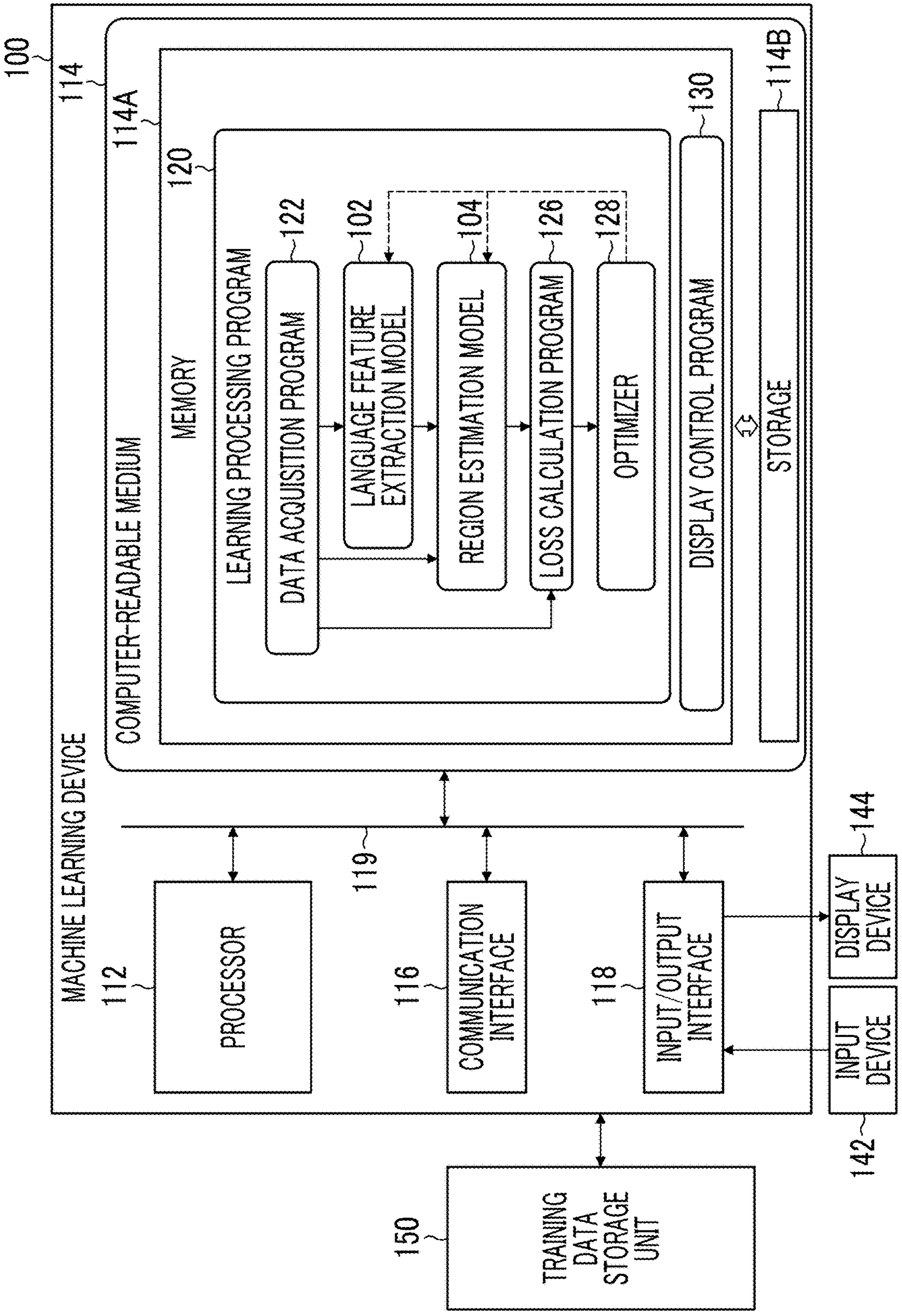
FIG. 13 is a block diagram showing an example of a hardware configuration of the machine learning device.

FIG. 13 is a block diagram showing an example of a hardware configuration of the machine learning device 100. The machine learning device 100 comprises a processor 112, a computer-readable medium 114, which is a non-transitory tangible object, a communication interface 116, an input/output interface 118, and a bus 119. The processor 112 is connected to the computer-readable medium 114, the communication interface 116, and the input/output interface 118 via the bus 119.

A form of the machine learning device 100 is not particularly limited and may be a server, a workstation, a personal computer, or the like.

The processor 112 includes a central processing unit (CPU). The processor 112 may include a graphics processing unit (GPU). The computer-readable medium 114 includes a memory 114A which is a main storage device and a storage 114B which is an auxiliary storage device. The computer-readable medium 114 may be, for example, a semiconductor memory, a hard disk drive (HDD) device or a solid state drive (SSD) device, or a plurality of combinations thereof.

The machine learning device 100 may further comprise an input device 142 and a display device 144. The input device 142 is configured with, for example, a keyboard, a mouse, a multi-touch panel, another pointing device, a voice input device, or an appropriate combination thereof. The display device 144 is configured with, for example, a liquid crystal display, an organic electro-luminescence (OEL) display, a projector, or an appropriate combination thereof. The input device 142 and the display device 144 are connected to the processor 112 via the input/output interface 118.

The machine learning device 100 may be connected to an electric telecommunication line (not shown) via the communication interface 116. The electric telecommunication line may be a wide area communication line, a local area communication line, or a combination thereof.

The machine learning device 100 is communicably connected to an external device such as a training data storage unit 150 via the communication interface 116. The training data storage unit 150 includes a storage in which a training dataset including a plurality of pieces of training data TDj is stored. The training data storage unit 150 may be constructed in the storage 114B within the machine learning device 100.

The computer-readable medium 114 stores a plurality of programs including a learning processing program 120 and a display control program 130, data, and the like. The term "program" includes the concept of a program module. The processor 112 executes a command of the program stored in the computer-readable medium 114 to function as various processing units.

The learning processing program 120 includes a command to acquire the training data TDj and to execute learning processing of the language feature extraction model 102 and the region estimation model 104. That is, the learning processing program 120 includes a data acquisition program 122, the language feature extraction model 102, the region estimation model 104, a loss calculation program 126, and an optimizer 128. The data acquisition program 122 includes a command to execute processing of acquiring the training data TDj from the training data storage unit 150.

The loss calculation program 126 includes a command to execute processing of calculating a loss indicating an error between the estimated region information PAj indicated by the information indicating the position of the lesion region output from the region estimation model 104 and the position information TPj of the correct answer corresponding to the finding sentence TXj input to the language feature extraction model 102. The optimizer 128 includes a command to execute processing of calculating the update amount of the parameter of each model of the region estimation model 104 and the language feature extraction model 102 from the calculated loss, and of updating the parameter of each model.

The display control program 130 includes a command to generate a signal for display required for display output to the display device 144 and to execute display control of the display device 144.

Outline of Machine Learning Method

Figure 14:
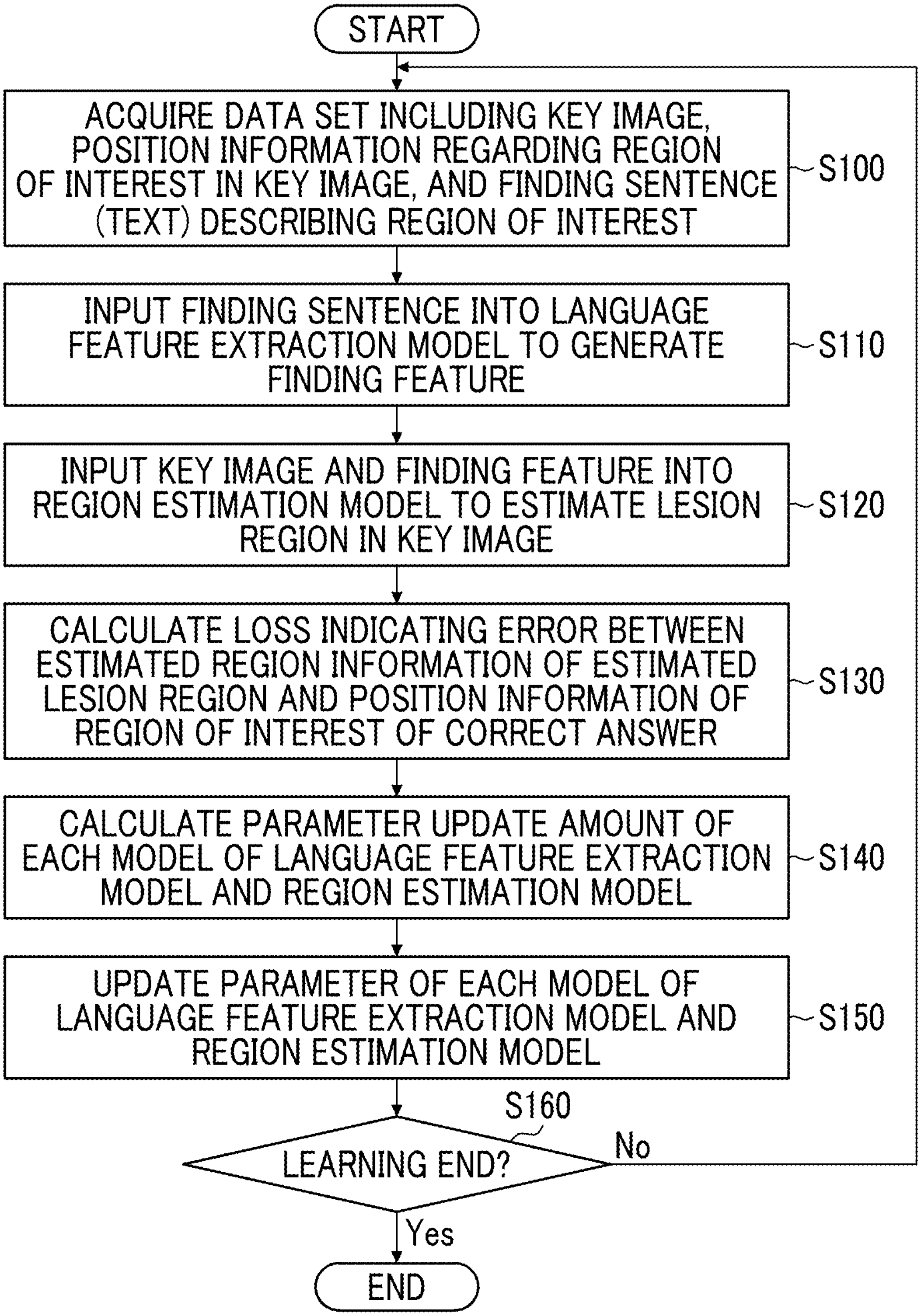
FIG. 14 is a flowchart showing an example of a machine learning method executed by the machine learning device.

FIG. 14 is a flowchart showing an example of a machine learning method executed by the machine learning device 100. Before the flowchart of FIG. 14 is executed, a plurality of sets of the training data TDj, which is a set of pieces of data in which the key image IMj for training, the finding sentence TXj which is a text describing a certain region of interest ROIj in the key image IMj, and the position information TPj regarding the region of interest ROIj are associated with each other, are prepared to prepare a dataset for training.

In step S100, the processor 112 acquires, from the dataset for training, a data set including the key image IMj, the position information TPj regarding the region of interest ROIj in the key image IMj, and the finding sentence TXj describing the region of interest ROIj.

In step S110, the processor 112 inputs the finding sentence TXj into the language feature extraction model 102 and causes the language feature extraction model 102 to extract the finding feature LFVj indicating the feature amount of the finding sentence TXj to obtain an output of the finding feature LFVj from the language feature extraction model 102. The finding feature LFVj is expressed by the language feature vector obtained by converting the finding sentence TXj into the feature vector.

In step S120, the processor 112 inputs the finding feature LFVj output by the language feature extraction model 102 and the key image IMj associated with the finding sentence TXj into the region estimation model 104 and causes the region estimation model 104 to estimate the region of interest (lesion region) in the key image IMj referred to in the input finding sentence TXj. The region estimation model 104 outputs the estimated region information PAj estimated from the input finding feature LFVj and key image IMj.

In step S130, the processor 112 calculates a loss indicating an error between the estimated region information PAj of the lesion region estimated by the region estimation model 104 and the position information TPj of the region of interest ROIj of the correct answer.

In step S140, the processor 112 calculates the parameter update amount of each model of the language feature extraction model 102 and the region estimation model 104 to minimize the loss.

In step S150, the processor 112 updates the parameter of each model of the language feature extraction model 102 and the region estimation model 104 in accordance with the calculated parameter update amount. The training of each model to minimize the loss means training of each model such that the estimated lesion region estimated by the region estimation model 104 matches the region of interest ROIj of the correct answer (such that error between the regions becomes small). The operations of steps S100 to S150 may be performed in a mini-batch unit.

After step S150, in step S160, the processor 112 determines whether or not to end the learning. An end condition of the learning may be determined based on a value of the loss or may be determined based on the number of updates of the parameter. As for a method based on the value of the loss, for example, the end condition of the learning may include that the loss converges within a prescribed range.

Further, as for a method based on the number of updates, for example, the end condition of the learning may include that the number of updates reaches a prescribed number of times. Alternatively, a dataset for performance evaluation of the model may be prepared separately from the training data, and whether or not to end the learning may be determined based on an evaluation value using the data for evaluation.

In a case where No determination is made in a determination result in step S160, the processor 112 returns to step S100 and continues the learning processing. On the other hand, in a case where Yes determination is made in the determination result in step S160, the processor 112 ends the flowchart of FIG. 14.

The learned (trained) language feature extraction model 102 generated in this manner is a model that may receive the input of the finding sentence and output the finding feature (feature vector) in which the position information regarding the lesion region (region of interest) in the image referred to in the finding sentence is embedded. That is, the information required to specify the position related to the lesion region in the image is embedded in the finding feature output by the language feature extraction model 102. The machine learning method executed by the machine learning device 100 can be understood as a method of generating the language feature extraction model 102 that outputs the language feature vector including the information specifying the position of the lesion region in the image described in the finding sentence.

Image Feature Extraction Model and Cross-Modal Feature Integration Model

The object information acquisition unit 34 may comprise an image feature extraction model. The image feature extraction model is a learned model that has been trained to receive inputs of a key image and position information regarding a region of interest in the key image and to output an image feature indicating a feature amount of the key image.

The correspondence determination unit 40 may comprise a cross-modal feature integration model. The cross-modal feature integration model is a learned model that has been trained to discriminate a correspondence relationship between an image provided with position information regarding a region of interest in the image and a finding sentence describing the region of interest.

Figure 15:
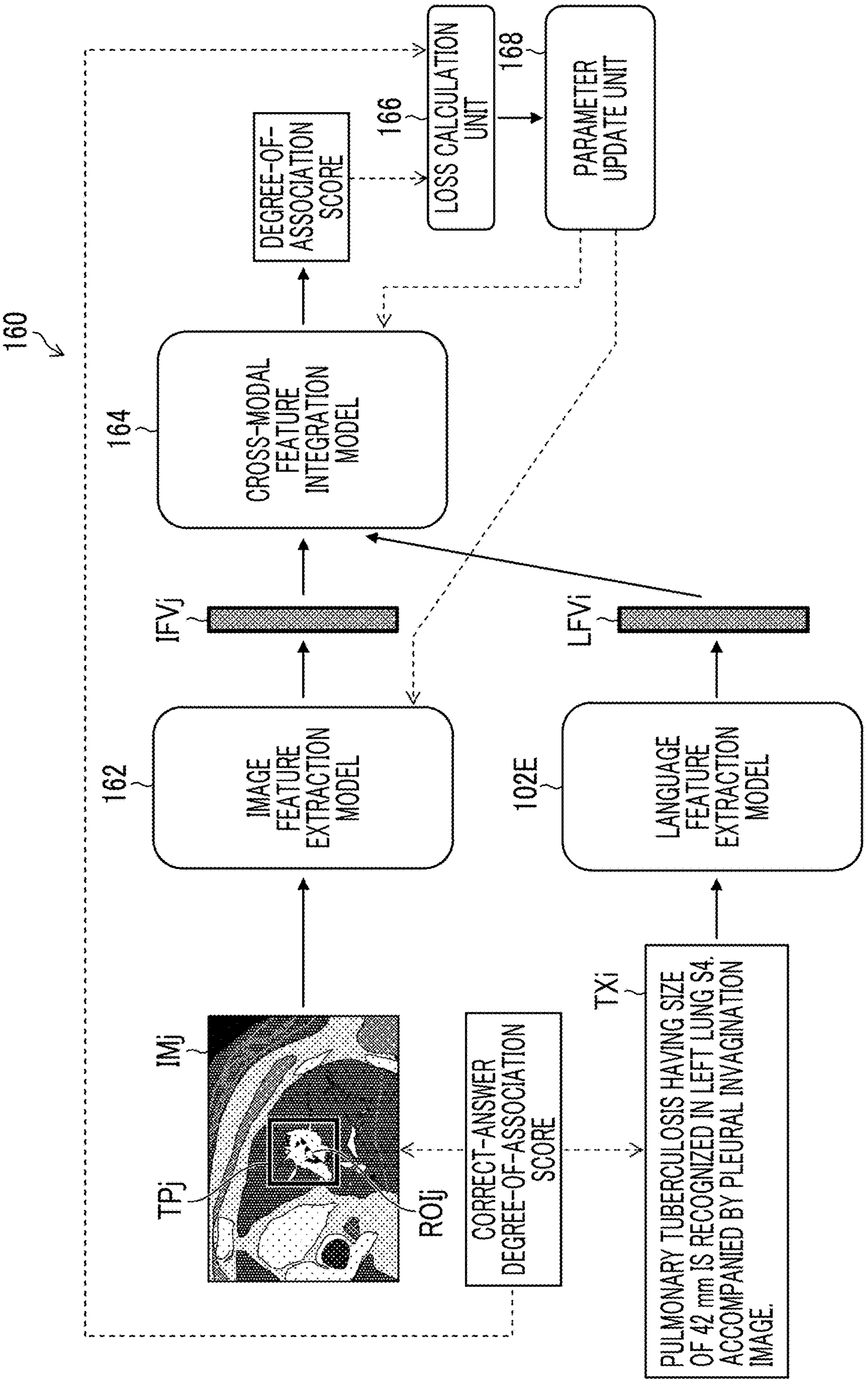
FIG. 15 is a block diagram schematically showing a functional configuration of the machine learning device that causes an image feature extraction model and a cross-modal feature integration model to learn.

FIG. 15 is a block diagram schematically showing a functional configuration of a machine learning device 160 that causes the image feature extraction model and the cross-modal feature integration model to learn using the learned language feature extraction model. The machine learning device 160 may be the same device as the machine learning device 100 or may be the same device as the information processing apparatus for medical 20.

The machine learning device 160 includes a language feature extraction model 102E, an image feature extraction model 162, a cross-modal feature integration model 164, a loss calculation unit 166, and a parameter update unit 168.

The dataset for training may be the same as the dataset used in the machine learning device 100. As the image feature extraction model 162, for example, CNN is applied. The image feature extraction model 162 receives inputs of the key image IMj and the position information TPj regarding the region of interest ROIj in the key image IMj and outputs an image feature IFVj indicating the feature amount of the key image IMj. The image feature IFVj may be expressed by the image feature vector obtained by converting the key image IMj into a feature vector. The image feature IFVj may be a feature map of a plurality of channels.

The language feature extraction model 102E is a learned model trained to receive an input of the finding sentence TXi and output a corresponding finding feature LFVi. The finding sentence TXi input to the language feature extraction model 102E is not limited to a case where the finding sentence TXj (i=j) is associated with the key image IMj and may also be a case where the finding sentence TXj (i≠j) is not associated with the key image IMj.

The cross-modal feature integration model 164 receives inputs of the image feature IFVj and the finding feature LFVj, and outputs a degree-of-association score indicating the relevance between the two features. The degree-of-association score may be a numerical value indicating a degree of relevance or may be a numerical value in a range of 0 to 1 as "0" in a case where there is no relevance and "1" in a case where there is relevance to indicate the degree of certainty of the relevance.

The loss calculation unit 166 calculates a loss indicating an error between the degree-of-association score output from the cross-modal feature integration model 164 and a correct-answer degree-of-association score. In a case where a combination of the key image IMj and the finding sentence TXi (i=j) associated with the key image IMj is input to the image feature extraction model 162 and the language feature extraction model 102E, the correct-answer degree-of-association score may be set as "1". On the other hand, in a case where a combination of the key image IMj and an irrelevant finding sentence TXi (i≠j) not associated with the key image IMj is input to the image feature extraction model 162 and the language feature extraction model 102E, the correct-answer degree-of-association score may be set as "0".

The parameter update unit 168 calculates the update amount of the parameter of each model of the cross-modal feature integration model 164 and the image feature extraction model 162 such that the loss calculated by the loss calculation unit 166 is minimized, and updates the parameter of each model according to the calculated update amount.

A hardware configuration of the machine learning device 160 may be the same as the machine learning device 100 shown in FIG. 13. The machine learning device 160 includes the cross-modal feature integration model 164 instead of the region estimation model 104 in FIG. 13. The machine learning device 160 differs from the machine learning device 100 in a loss function of the loss calculated by the loss calculation program 126 and a model whose parameter is updated by the optimizer 128.

Outline of Machine Learning Method

Figure 16:
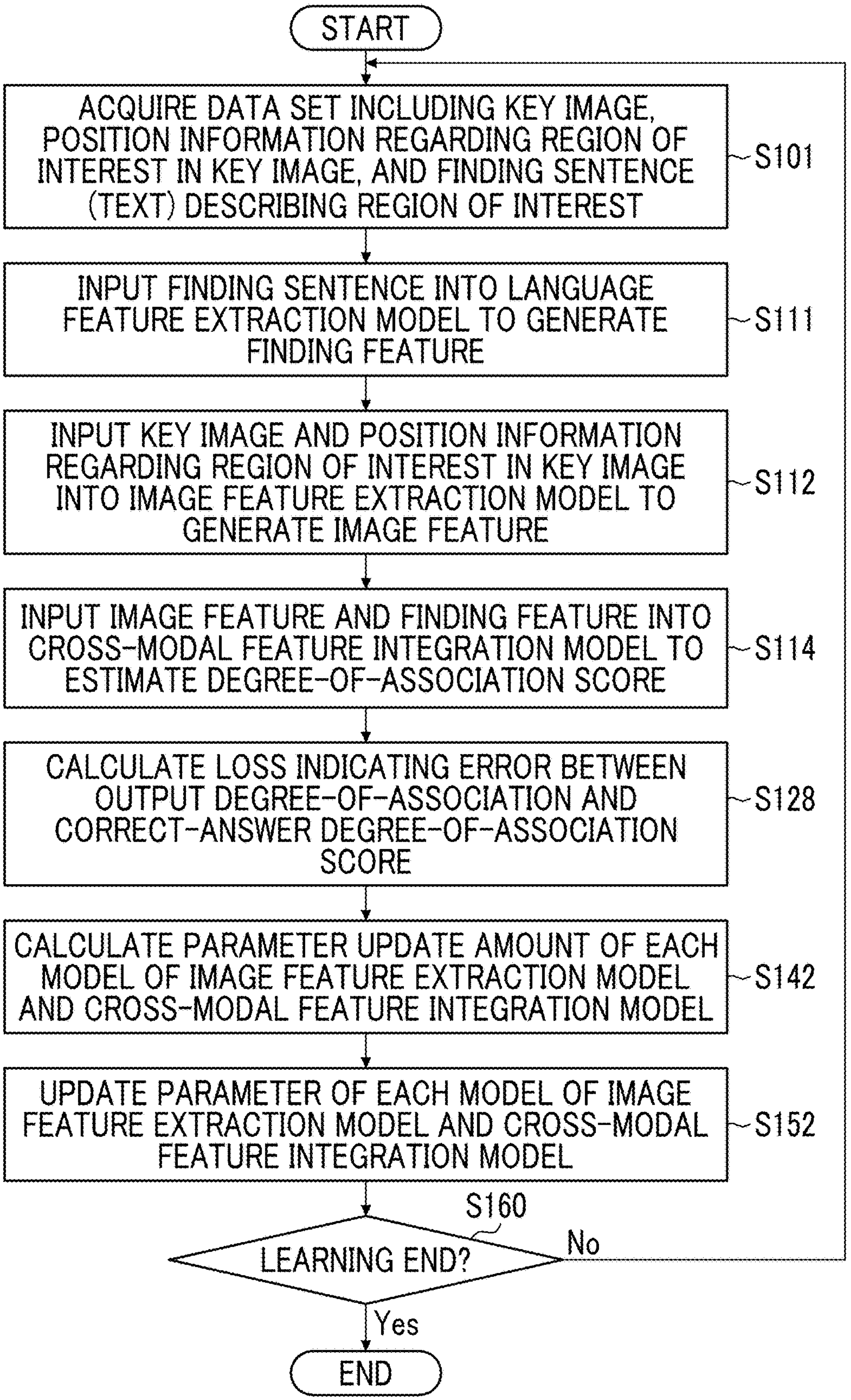
FIG. 16 is a flowchart showing an example of the machine learning method executed by the machine learning device.

FIG. 16 is a flowchart showing an example of the machine learning method executed by the machine learning device 160. In step S101, the processor 112 acquires, from the dataset for training, a data set of the key image IMj, the position information TPj regarding the region of interest ROIj in the key image IMj, and the finding sentence TXi describing the region of interest ROIj. In the data set acquired in this case, the processor 112 acquires "1" as the correct-answer degree-of-association score in a case where i=j and acquires "0" as the correct-answer degree-of-association score in a case where i≠j.

In step S111, the processor 112 inputs the finding sentence TXi into the language feature extraction model 102E and causes the language feature extraction model 102E to extract the finding feature LFVi.

In step S112, the processor 112 inputs the key image IMj and the position information TPj regarding the region of interest ROIj in the key image IMj into the image feature extraction model 162, and causes the image feature extraction model 162 to extract the image feature IFVj.

In step S114, the processor 112 inputs the image feature IFVj, which is output from the image feature extraction model 162, and the finding feature LFVi, which is output from the language feature extraction model 102E, into the cross-modal feature integration model 164, and causes the cross-modal feature integration model 164 to estimate the degree-of-association score. The image feature extraction model 162 is caused to extract the image feature IFVj.

Thereafter, in step S128, the processor 112 calculates a loss indicating an error between the degree-of-association score (estimated value) output from the cross-modal feature integration model 164 and the correct-answer degree-of-association score.

In step S142, the processor 112 calculates the parameter update amount of each model of the image feature extraction model 162 and the cross-modal feature integration model 164 such that the calculated loss is minimized.

In step S152, the processor 112 updates the parameter of each model of the image feature extraction model 162 and the cross-modal feature integration model 164 according to the calculated parameter update amount.

The operations of steps S101 to S152 shown in FIG. 16 may be performed in a mini-batch unit.

After step S152, in step S160, the processor 112 determines whether or not to end the learning.

In a case where No determination is made in a determination result in step S160, the processor 112 returns to step S101 and continues the learning processing. On the other hand, in a case where Yes determination is made in the determination result in step S160, the processor 112 ends the flowchart of FIG. 16.

With the causing of each model to learn in this manner, it is possible to construct a degree-of-association determination artificial intelligence (AI) that may accurately determine whether or not the input image corresponds to the finding sentence (whether or not there is relevance).

Specification of Region of Interest in Medical Image

Configuration of Object Information Acquisition Unit

The object information acquisition unit 34 may analyze the medical image, which is an original image serving as a creation source of the key image, to acquire the object information. Here, a method will be described in which the region of interest of the medical image serving as the creation source of the key image is specified based on the region of interest which is the lesion region of the key image.

Figure 17:
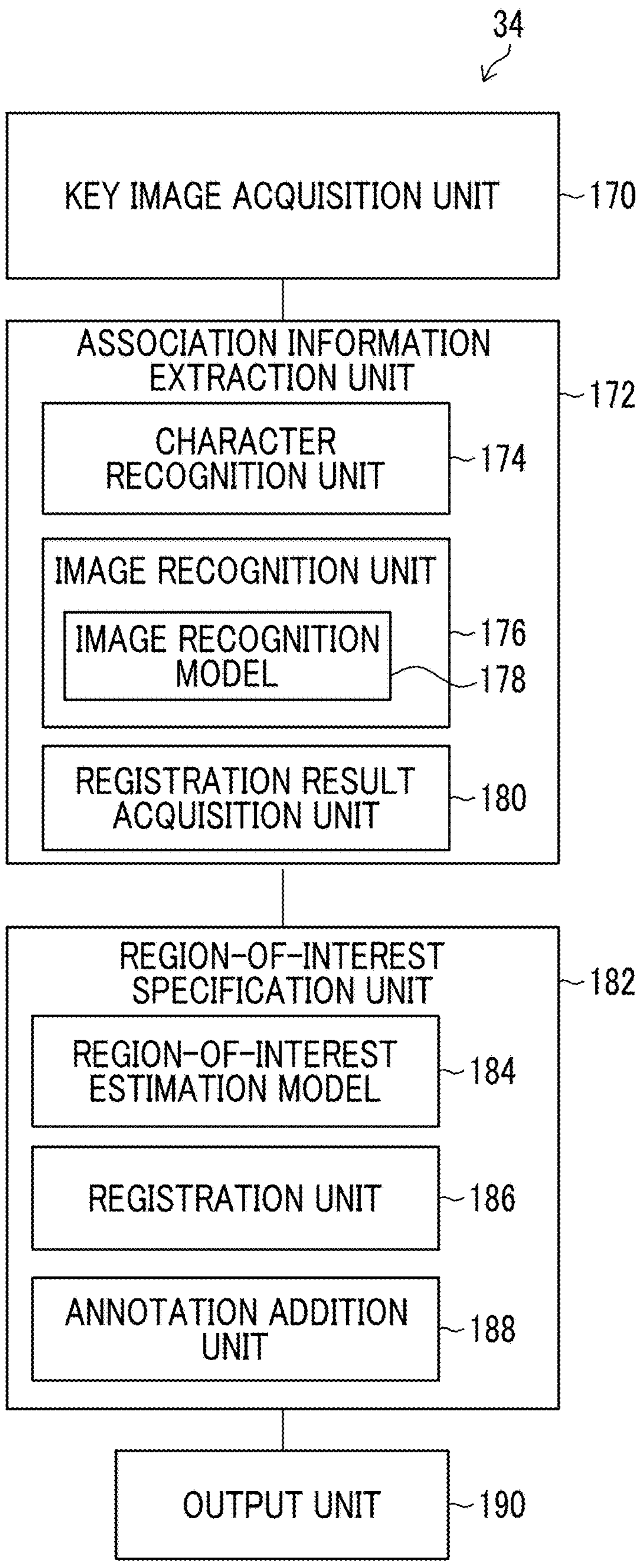
FIG. 17 is a block diagram showing a functional configuration of an object information acquisition unit.

FIG. 17 is a block diagram showing a functional configuration of the object information acquisition unit 34. As shown in FIG. 17, the object information acquisition unit 34 comprises a key image acquisition unit 170, an association information extraction unit 172, a region-of-interest specification unit 182, and an output unit 190.

The key image acquisition unit 170 acquires the key image received by the image acquisition unit 32 of the information processing apparatus for medical 20.

The association information extraction unit 172 analyzes the key image to extract association information with the medical image which is the creation source of the key image. That is, the association information is information for associating the key image with the medical image serving as the creation source of the key image. The association information is, for example, information that is shown in the key image separately from the subject. The association information includes, for example, at least one of a series number, a slice number, a window width, a window level, or an annotation of the medical image serving as the creation source of the key image. The association information may be a result of registration between the key image and the medical image serving as the creation source of the key image. The association information extraction unit 172 includes a character recognition unit 174, an image recognition unit 176, and a registration result acquisition unit 180.

The character recognition unit 174 analyzes a character in the key image by character recognition of a known method such as optical character recognition (OCR) to extract the association information. The association information extracted by the character recognition unit 174 may include at least one of a window width, a window level, a slice number, or a series number of the key image.

The image recognition unit 176 performs image recognition of the key image to extract the association information. The association information extracted by the image recognition unit 176 may include at least one of the window width, the window level, or the annotation of the key image. The image recognition unit 176 comprises an image recognition model 178. The image recognition model 178 that extracts the window width or the window level of the key image is a classification model or a regression model using the CNN. Further, the image recognition model 178 that recognizes the annotation of the key image is a segmentation model or a detection model to which the convolutional neural network is applied. The image recognition unit 176 may comprise a plurality of image recognition models 178 among the classification model, the regression model, the segmentation model, and the detection model. The image recognition model 178 is stored in the memory 20B.

Further, the image recognition unit 176 detects the annotation added to the key image. The annotation detected by the image recognition unit 176 may include at least one of a circle, a rectangle, an arrow, a line segment, a point, or a scribble.

The registration result acquisition unit 180 acquires the result of registration between the key image and the medical image by a registration unit 186 described below.

The region-of-interest specification unit 182 specifies the region of interest based on the association information extracted by the association information extraction unit 172. The region-of-interest specification unit 182 uses the association information to, for example, first estimate a position corresponding to the key image in the medical image serving as the creation source of the key image and then specify the region of interest of the medical image.

The region-of-interest specification unit 182 may specify the region of interest from a two-dimensional image or may specify the region of interest from a three-dimensional image. The region of interest to be specified may be a two-dimensional region or a three-dimensional region.

The region-of-interest specification unit 182 includes a region-of-interest estimation model 184, a registration unit 186, and an annotation addition unit 188. The region-of-interest estimation model 184 is a deep learning model that outputs, in a case where an image is provided as input, the position of the region of interest in the input image. The region-of-interest estimation model 184 may be a learned model to which the CNN is applied. The region-of-interest estimation model 184 is stored in the memory 20B.

The registration unit 186 performs the registration between the key image and the medical image serving as the creation source of the key image. The registration between the key image and the medical image serving as the creation source of the key image means making respective pixels of both images showing the same subject, such as an organ, correspond to each other. The result of registration between the key image and the medical image by the registration unit 186 includes a correspondence relationship between the pixel of the key image and the pixel of the medical image. The annotation addition unit 188 adds the annotation to the medical image serving as the creation source of the key image.

The output unit 190 outputs the region of interest specified by the region-of-interest specification unit 182. The output region of interest may be at least one of a mask, a bounding box, or a heat map, which is assigned to the medical image serving as the creation source of the key image.

Medical Image Analysis Method

Figure 18:
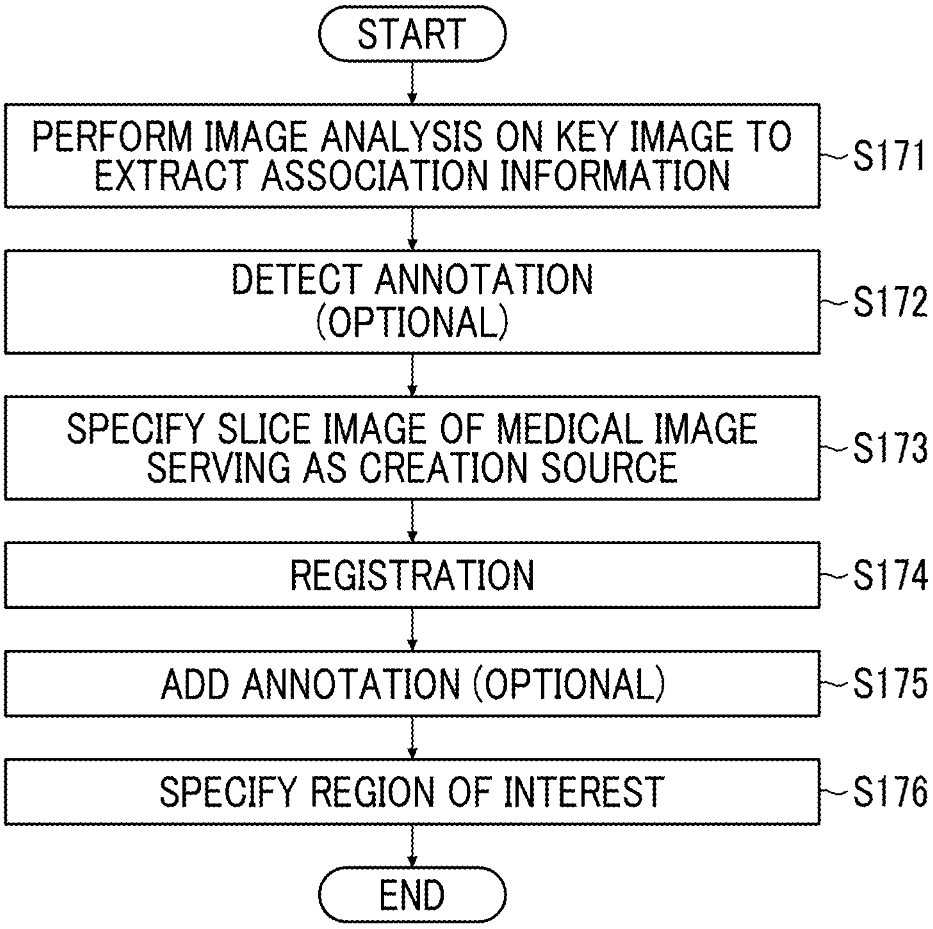
FIG. 18 is a flowchart showing a medical image analysis method by the object information acquisition unit.

FIG. 18 is a flowchart showing a medical image analysis method by the object information acquisition unit 34. The medical image analysis method is a method of specifying the region of interest of the medical image serving as the creation source of the key image.

In step S171, the key image acquisition unit 170 acquires the key image received by the image acquisition unit 32 of the information processing apparatus for medical 20. The association information extraction unit 172 extracts, from the key image, the association information necessary for association with the medical image serving as the creation source of the key image. Here, the image recognition unit 176 extracts the association information from the key image using the image recognition model 178. Further, the character recognition unit 174 extracts the association information from the key image using the OCR.

In step S172, in a case where the annotation is added to the key image acquired in step S171, the image recognition unit 176 detects the annotation from the key image.

In step S173, the region-of-interest specification unit 182 specifies a slice image of the medical image serving as the creation source, which is at the same position as the key image, based on the slice number in the association information extracted in step S171. In step S171, in a case where the slice number cannot be extracted, the slice image at the same position as the key image is specified by a known method.

In step S174, the registration unit 186 performs the registration between the key image and the slice image specified in step S173. Since the key image may be cropped or rotated from the slice image of the medical image serving as the creation source, the registration may be required.

In step S175, in a case where the annotation is added to the key image acquired in step S171, the annotation addition unit 188 adds the annotation to the slice image specified in step S173. The annotation addition unit 188 can add the annotation at the same position of the slice image as the position of the annotation of the key image with the registration in step S174.

In step S176, the region-of-interest specification unit 182 specifies the region of interest of the slice image based on the annotation added in step S175. Here, the region-of-interest specification unit 182 specifies the region of interest using the region-of-interest estimation model 184. A result of specifying the region of interest may be at least one of a mask, a bounding box, or a heat map. The output unit 190 outputs the specified region of interest.

In this manner, with the addition of the annotation of the key image to the slice image serving as the creation source of the key image and estimation of the region of interest based on the annotation, it is possible to specify the region of interest of the slice image. Therefore, it is possible to specify the region of interest of the medical image serving as the creation source.

Here, the case has been described in which the annotation is added to the key image acquired in step S171, but the region-of-interest estimation model 184 can estimate the region of interest from the key image in which the annotation is not included.

Others

The information processing apparatus for medical, the information processing method for medical, and the information processing program for medical according to the present embodiment can also be applied to an information processing apparatus, an information processing method, and an information processing program that use a natural image other than the medical image.

For example, it can be applied to the creation of a report on social infrastructure facilities such as transportation, electricity, gas, and water supply. In this case, it is possible to acquire information regarding an object shown in one or more received images of the infrastructure facility, acquire information described in one or more received sentences related to the infrastructure facility, determine the presence or absence of the correspondence between the image and the sentence based on the information regarding the object and the described information, and execute processing of assisting in creating a document including the image and the sentence based on the presence or absence of the correspondence.

The technical scope of the present invention is not limited to the range described in the above-described embodiments. The configurations and the like in each embodiment can be appropriately combined between the respective embodiments without departing from the gist of the present invention.

EXPLANATION OF REFERENCES

- 10: information processing system for medical
- 12: medical image examination device
- 14: medical image database
- 16: user terminal device
- 16A: input device
- 16B: display
- 18: interpretation report database
- 20: information processing apparatus for medical
- 20A: processor
- 20B: memory
- 20C: communication interface
- 22: network
- 32: image acquisition unit
- 34: object information acquisition unit
- 36: sentence acquisition unit
- 38: description information acquisition unit
- 40: correspondence determination unit
- 42: assistance processing execution unit
- 100: machine learning device
- 102: language feature extraction model
- 102E: language feature extraction model
- 104: region estimation model
- 106: loss calculation unit
- 108: parameter update unit
- 112: processor
- 114: computer-readable medium
- 114A: memory
- 114B: storage
- 116: communication interface
- 118: input/output interface
- 119: bus
- 120: learning processing program
- 122: data acquisition program
- 126: loss calculation program

128: optimizer
130: display control program
142: input device
144: display device
150: training data storage unit
160: machine learning device
162: image feature extraction model
164: cross-modal feature integration model
166: loss calculation unit
168: parameter update unit
170: key image acquisition unit
172: information extraction unit
174: character recognition unit
176: image recognition unit
178: image recognition model
180: result acquisition unit
182: region-of-interest specification unit
184: region-of-interest estimation model
186: registration unit
188: annotation addition unit
190: output unit
A1: lesion region
A2: lesion region
A3: lesion region
D1: display region
D2: display region
FL1: frame
IK1: key image
IK2: key image
IK3: key image
IK11: key image
IK12: key image
IK13: key image
IK21: key image
IK22: key image
IK31: key image
IMj: key image
L1: sentence
L2: sentence
LFVj: finding feature
MK1: marker
NF1: figure number
NF2: figure number
PAj: estimated region information
ROIi: region of interest
ROIj: region of interest
RP1: interpretation report
RP2: interpretation report
RP3: interpretation report
SN1: finding sentence
SN2: finding sentence
SN3: finding sentence
SN4: finding sentence
SN5: finding sentence
SN6: finding sentence
SN11: finding sentence
SN12: finding sentence
SN21: finding sentence
SN31: finding sentence
SN32: finding sentence
S1 to S6: steps of information processing method for medical
S101 to S160: steps of machine learning method
S171 to S176: steps of medical image analysis method
TDj: training data
TPj: position information
TXi: finding sentence
TXj: finding sentence

What is claimed is:

1. An information processing apparatus comprising:

at least one processor; and at least one memory that stores a command to be executed by the at least one processor, wherein the at least one processor is configured to:

acquire information regarding an object shown in one or more received images by inputting the received image into an image feature extraction model configured to convert the received image into an image feature vector indicating the information regarding the object;

acquire information described in one or more received sentences by inputting the received sentence into a language feature extraction model configured to convert the received sentence into a language feature vector indicating the described information;

determine presence or absence of correspondence between the image and the sentence based on the information regarding the object and the described information by inputting the image feature vector output from the image feature extraction model and the language feature vector output from the language feature extraction model into a cross-modal feature integration model configured to output a degree of certainty indicating certainty of correspondence between the information regarding the object and the described information; and execute processing of assisting in creating a document including the image and the sentence based on the presence or absence of the correspondence, wherein the processing is processing of assigning a figure number to the image out of the sentence and the image, which are determined to have the correspondence.

2. The information processing apparatus according to claim 1, wherein the processing is processing of issuing a warning in a case where the image corresponding to the sentence is not present.

3. The information processing apparatus according to claim 1, wherein the processing is processing of issuing a warning in a case where the image corresponding to the sentence is not present and a degree of importance of the sentence, which indicates a degree to which an image corresponding to the sentence is necessary, is equal to or larger than a threshold value.

4. The information processing apparatus according to claim 1, wherein the processing is processing of issuing a warning in a case where the sentence corresponding to the image is not present.

5. The information processing apparatus according to claim 1, wherein the processing is processing of rearranging, based on an order of one of the sentences and the images determined to have the correspondence, an order of the other.

6. The information processing apparatus according to claim 5, wherein the processing is processing of rearranging an order of the images based on an order of the sentences.

7. The information processing apparatus according to claim 1, wherein the processing of assigning the figure number is processing of assigning a figure number in an order in which the object shown in the image appears in the corresponding sentence.

8. The information processing apparatus according to claim 7, wherein the processing is processing of assigning a figure number assigned to the image to the sentence out of the sentence and the image, which are determined to have the correspondence.

9. The information processing apparatus according to claim 8, wherein the processing is processing of assigning a figure number to a corresponding portion of the sentence.

10. The information processing apparatus according to claim 1, wherein the at least one processor is configured to:

execute the processing each time any one of an input of the image or an input of the sentence is received.

11. The information processing apparatus according to claim 10, wherein there are provided a first mode in which the processing is executed each time any one of the input of the image or the input of the sentence is received and a second mode in which the processing is executed after inputs of all the images and all the sentences are received.

12. The information processing apparatus according to claim 1, wherein the at least one processor is configured to:

acquire the degree of certainty indicating certainty of correspondence between the information regarding the object and the described information; and determine whether or not the image and the sentence correspond to each other based on the degree of certainty.

13. The information processing apparatus according to claim 1, wherein the at least one processor is configured to:

analyze the received image or an original image serving as a creation source of the received image to acquire the information regarding the object.

14. The information processing apparatus according to claim 1, wherein the image is a key image based on a medical image.

15. The information processing apparatus according to claim 14, wherein the object includes at least one of an organ or a tumor, and the information regarding the object includes at least one of a size, a property, a disease name, a position, or a feature amount.

16. An information processing method comprising:

by at least one processor, acquiring information regarding an object shown in one or more received images by inputting the received image into an image feature extraction model configured to convert the received image into an image feature vector indicating the information regarding the object;

acquiring information described in one or more received sentences by inputting the received sentence into a language feature extraction model configured to convert the received sentence into a language feature vector indicating the described information;

determining presence or absence of correspondence between the image and the sentence based on the information regarding the object and the described information by inputting the image feature vector output from the image feature extraction model and the language feature vector output from the language feature extraction model into a cross-modal feature integration model configured to output a degree of certainty indicating certainty of correspondence between the information regarding the object and the described information; and executing processing of assisting in creating a document including the image and the sentence based on the presence or absence of the correspondence, wherein the processing is processing of assigning a figure number to the image out of the sentence and the image, which are determined to have the correspondence.

17. A non-transitory, computer-readable tangible recording medium which records thereon a program for causing, when read by a computer, the computer to execute the information processing method according to claim 16.

* * * * *